(12) United States Patent
Phan et al.

(10) Patent No.: US 12,708,382 B2
(45) Date of Patent: Aug. 18, 2026

(54) LESION CROSSING SHOCK WAVE CATHETER

(71) Applicant: Shockwave Medical, Inc., Santa Clara, CA (US)

(72) Inventors: Huy Phan, Santa Clara, CA (US); Hoa Nguyen, Santa Clara, CA (US); Chi Long, Santa Clara, CA (US); Todd Jenkins, San Jose, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 316 days.

(21) Appl. No.: 18/632,713

(22) Filed: Apr. 11, 2024

(65) Prior Publication Data

US 2024/0268842 A1 Aug. 15, 2024

Related U.S. Application Data

(62) Division of application No. 17/021,905, filed on Sep. 15, 2020, now Pat. No. 12,274,460.

(Continued)

(51) Int. Cl.
*A61B 17/22* (2006.01)

(52) U.S. Cl.
CPC .................. *A61B 17/22004* (2013.01); *A61B 2017/22001* (2013.01); *A61B 2017/22044* (2013.01);

(Continued)

(58) Field of Classification Search
CPC .......... A61B 17/22004; A61B 17/2202; A61B 17/22022; A61B 17/22012;

(Continued)

(56) References Cited

U.S. PATENT DOCUMENTS 2,916,647 A 12/1959 George
3,412,288 A 11/1968 Ostrander (Continued)

FOREIGN PATENT DOCUMENTS

AU 2009313507 B2 11/2014
AU 2013284490 B2 5/2018

(Continued)

OTHER PUBLICATIONS

21 C.F.R. 870.5100 Title 21, vol. 8 Apr. 1, 2018 pp. 1-2.

(Continued)

*Primary Examiner* — Sarah A Long
*Assistant Examiner* — Lauren Dubose
(74) *Attorney, Agent, or Firm* — Morrison & Foerster LLP

(57) ABSTRACT

The present invention provides a catheter for treating occlusions in blood vessels. The catheter includes at least one electrode pair positioned inside of a flexible angioplasty balloon at the distal end of the catheter. In some designs, the electrode pairs are arranged in a low-profile or coplanar configuration, reducing the diameter of the distal end of the device and permitting treatment of tight and hard-to-cross occlusions. The flexible angioplasty balloon has an extremely low profile and does need to be folded before insertion of the catheter into the cardiovascular system. During treatment, the balloon can be expanded a relatively small amount sufficient to immerse the electrode pairs in a conductive fluid before generating shock waves across the electrodes to treat the occlusion. The balloon can be made of material having elastomeric properties such that it returns to its original low profile configuration when it is deflated following treatment.

15 Claims, 13 Drawing Sheets

Related U.S. Application Data

(60) Provisional application No. 62/904,847, filed on Sep. 24, 2019.

(52) U.S. Cl.
CPC ............... *A61B 2017/22045* (2013.01); *A61B 2017/22067* (2013.01); *A61B 2017/22071* (2013.01); *A61B 2017/22094* (2013.01)

(58) Field of Classification Search
CPC ...... A61B 17/22029; A61B 17/320068; A61B 2017/22021; A61B 2017/22025; A61B 2017/22067; A61B 2017/22094; A61B 2017/22014; A61B 2018/1405; A61M 37/0092
See application file for complete search history.

(56) References Cited

U.S. PATENT DOCUMENTS 3,413,976 A 12/1968 Voolfovich
3,524,101 A 8/1970 Barbini
3,583,766 A 6/1971 Padberg, Jr.
3,785,382 A 1/1974 Schmidt et al.
3,902,499 A 9/1975 Shene
3,942,531 A 3/1976 Hoff et al.
4,027,674 A 6/1977 Tessler et al.
4,030,505 A 6/1977 Tessler
4,445,509 A 5/1984 Auth
4,662,126 A 5/1987 Malcolm
4,662,375 A 5/1987 Hepp et al.
4,671,254 A 6/1987 Fair
4,685,458 A 8/1987 Leckrone
4,741,405 A 5/1988 Moeny et al.
4,809,682 A 3/1989 Forssmann et al.
4,813,934 A 3/1989 Engelson et al.
4,878,495 A 11/1989 Grayzei
4,890,603 A 1/1990 Filler
4,900,303 A 2/1990 Lemeison
4,990,134 A 2/1991 Auth
4,994,032 A 2/1991 Sugiyama et al.
5,009,232 A 4/1991 Hassler et al.
5,046,503 A 9/1991 Schneiderman
5,057,103 A 10/1991 Davis
5,057,106 A 10/1991 Kasevich et al.
5,061,240 A 10/1991 Cherian
5,078,717 A 1/1992 Parins et al.
5,102,402 A 4/1992 Dror et al.
5,103,804 A 4/1992 Abele et al.
5,116,227 A 5/1992 Levy
5,152,767 A 10/1992 Sypal et al.
5,152,768 A 10/1992 Bhatta
5,154,722 A 10/1992 Filip et al.
5,176,675 A 1/1993 Watson et al.
5,195,508 A 3/1993 Muller et al.
5,231,976 A 8/1993 Wiksell
5,245,988 A 9/1993 Einars et al.
5,246,447 A 9/1993 Rosen et al.
5,254,121 A 10/1993 Manevitz et al.
5,281,231 A 1/1994 Rosen et al.
5,295,958 A 3/1994 Shturman
5,304,134 A 4/1994 Kraus et al.
5,321,715 A 6/1994 Trost
5,324,255 A 6/1994 Passafaro et al.
5,336,234 A 8/1994 Vigil et al.
5,362,309 A 11/1994 Carter
5,364,393 A 11/1994 Auth et al.
5,368,591 A 11/1994 Lennox et al.
5,395,335 A 3/1995 Jang
5,417,208 A 5/1995 Winkler
5,425,735 A 6/1995 Rosen et al.
5,431,173 A 7/1995 Chin et al.
5,454,809 A 10/1995 Janssen
5,472,406 A 12/1995 De La Torre et al.
5,582,578 A 12/1996 Zhong et al.
5,584,843 A 12/1996 Wulfman et al.
5,603,731 A 2/1997 Whitney
5,609,606 A 3/1997 O'Boyle
5,662,590 A 9/1997 De La Torre et al.
5,709,676 A 1/1998 Alt
5,846,218 A 12/1998 Brisken et al.
5,891,089 A 4/1999 Katz et al.
5,893,840 A 4/1999 Hull et al.
5,931,805 A 8/1999 Brisken
6,007,530 A 12/1999 Domhofer et al.
6,024,718 A 2/2000 Chen et al.
6,033,371 A 3/2000 Torre et al.
6,056,722 A 5/2000 Jayaraman
6,080,119 A 6/2000 Schwarze et al.
6,083,232 A 7/2000 Cox
6,090,104 A 7/2000 Webster et al.
6,113,560 A 9/2000 Simnacher
6,132,444 A 10/2000 Shturman et al.
6,146,358 A 11/2000 Rowe
6,186,963 B1 2/2001 Schwarze et al.
6,210,408 B1 4/2001 Chandrasekaran et al.
6,215,734 B1 4/2001 Moeny et al.
6,217,531 B1 4/2001 Reitmajer
6,267,747 B1 7/2001 Samson et al.
6,277,138 B1 8/2001 Levinson et al.
6,287,272 B1 9/2001 Brisken et al.
6,352,535 B1 3/2002 Lewis et al.
6,364,894 B1 4/2002 Healy et al.
6,367,203 B1 4/2002 Graham et al.
6,371,971 B1 4/2002 Tsugita et al.
6,398,792 B1 6/2002 O'Connor
6,406,486 B1 6/2002 De La Torre et al.
6,440,124 B1 8/2002 Esch et al.
6,494,890 B1 12/2002 Shturman et al.
6,514,203 B2 2/2003 Bukshpan
6,524,251 B2 2/2003 Rabiner et al.
6,589,253 B1 7/2003 Comish et al.
6,607,003 B1 8/2003 Wilson
6,638,246 B1 10/2003 Naimark et al.
6,652,547 B2 11/2003 Rabiner et al.
6,666,834 B2 12/2003 Restle et al.
6,689,089 B1 2/2004 Tiedtke et al.
6,736,784 B1 5/2004 Menne et al.
6,740,081 B2 5/2004 Hilal
6,755,821 B1 6/2004 Fry
6,939,320 B2 9/2005 Lennox
6,989,009 B2 1/2006 Lafontaine
7,066,904 B2 6/2006 Rosenthal et al.
7,087,061 B2 8/2006 Chernenko et al.
7,241,295 B2 7/2007 Maguire
7,309,324 B2 12/2007 Hayes et al.
7,389,148 B1 6/2008 Morgan
7,505,812 B1 3/2009 Eggers et al.
7,569,032 B2 8/2009 Naimark et al.
7,850,685 B2 12/2010 Kunis et al.
7,853,332 B2 12/2010 Olsen et al.
7,873,404 B1 1/2011 Patton
7,951,111 B2 5/2011 Drasler et al.
8,162,859 B2 4/2012 Schultheiss et al.
8,177,801 B2 5/2012 Kallok et al.
8,353,923 B2 1/2013 Shturman
8,556,813 B2 10/2013 Cioanta et al.
8,574,247 B2 11/2013 Adams et al.
8,728,091 B2 5/2014 Hakala et al.
8,747,416 B2 6/2014 Hakala et al.
8,888,788 B2 11/2014 Hakala et al.
8,956,371 B2 2/2015 Hawkins et al.
8,956,374 B2 2/2015 Hawkins et al.
9,005,216 B2 4/2015 Hakala et al.
9,011,462 B2 4/2015 Adams et al.
9,011,463 B2 4/2015 Adams et al.
9,044,618 B2 6/2015 Hawkins et al.
9,044,619 B2 6/2015 Hawkins et al.
9,072,534 B2 7/2015 Adams et al.
9,138,249 B2 9/2015 Adams et al.
9,198,825 B2 12/2015 Katragadda et al.
9,333,000 B2 5/2016 Hakala et al.
9,421,025 B2 8/2016 Hawkins et al.
9,433,428 B2 9/2016 Hakala et al.

(56) References Cited

U.S. PATENT DOCUMENTS 9,522,012 B2 12/2016 Adams
9,642,673 B2 5/2017 Adams et al.
9,730,715 B2 8/2017 Adams
9,993,292 B2 6/2018 Adams et al.
10,039,561 B2 8/2018 Adams et al.
10,118,015 B2 11/2018 De La Rama et al.
10,149,690 B2 12/2018 Hawkins et al.
10,154,799 B2 12/2018 Van Der Weide et al.
10,159,505 B2 12/2018 Hakala et al.
10,206,698 B2 2/2019 Hakala et al.
10,226,265 B2 3/2019 Ku et al.
10,517,620 B2 12/2019 Adams
10,517,621 B1 12/2019 Adams
10,555,744 B2 2/2020 Nguyen et al.
10,682,178 B2 6/2020 Adams et al.
10,702,293 B2 7/2020 Adams et al.
10,709,462 B2 7/2020 Nguyen et al.
10,959,743 B2 3/2021 Adams et al.
10,966,737 B2 4/2021 Nguyen
10,973,538 B2 4/2021 Hakala et al.
11,000,299 B2 5/2021 Hawkins et al.
11,076,874 B2 8/2021 Hakala et al.
11,337,713 B2 5/2022 Nguyen et al.
11,432,834 B2 9/2022 Adams
11,534,187 B2 12/2022 Bonutti
11,596,424 B2 3/2023 Hakala et al.
11,602,363 B2 3/2023 Nguyen
11,622,780 B2 4/2023 Nguyen et al.
11,696,799 B2 7/2023 Adams et al.
11,771,449 B2 10/2023 Adams et al.
11,950,793 B2 4/2024 Nguyen
12,232,754 B2 2/2025 Nguyen
12,232,755 B2 2/2025 Phan et al.
12,274,460 B2 4/2025 Phan et al.
2001/0044596 A1 11/2001 Jaafar
2002/0045890 A1 4/2002 Celliers et al.
2002/0077643 A1 6/2002 Rabiner et al.
2002/0082553 A1 6/2002 Duchamp
2002/0177889 A1 11/2002 Brisken et al.
2003/0004434 A1 1/2003 Greco et al.
2003/0060813 A1 3/2003 Loeb et al.
2003/0176873 A1 9/2003 Chernenko et al.
2003/0229370 A1 12/2003 Miller
2004/0006333 A1 1/2004 Arnold et al.
2004/0010249 A1 1/2004 Truckai et al.
2004/0044308 A1 3/2004 Naimark et al.
2004/0097963 A1 5/2004 Seddon
2004/0097996 A1 5/2004 Rabiner et al.
2004/0162508 A1 8/2004 Uebelacker
2004/0249401 A1 12/2004 Rabiner et al.
2004/0254570 A1 12/2004 Hadjicostis et al.
2005/0015953 A1 1/2005 Keidar
2005/0021013 A1 1/2005 Visuri et al.
2005/0059965 A1 3/2005 Eberl et al.
2005/0075662 A1 4/2005 Pedersen et al.
2005/0090888 A1 4/2005 Hines et al.
2005/0113722 A1 5/2005 Schultheiss
2005/0113822 A1 5/2005 Fuimaono et al.
2005/0171527 A1 8/2005 Bhola
2005/0228372 A1 10/2005 Truckai et al.
2005/0240146 A1 10/2005 Nash et al.
2005/0245866 A1 11/2005 Azizi
2005/0251131 A1 11/2005 Lesh
2006/0004286 A1 1/2006 Chang et al.
2006/0069424 A1 3/2006 Acosta et al.
2006/0074484 A1 4/2006 Huber
2006/0184076 A1 8/2006 Gm et al.
2006/0190022 A1 8/2006 Beyar et al.
2006/0221528 A1 10/2006 Li et al.
2007/0016112 A1 1/2007 Schultheiss et al.
2007/0088380 A1 4/2007 Hirszowicz et al.
2007/0129667 A1 6/2007 Tiedtke et al.
2007/0156129 A1 7/2007 Kovalcheck
2007/0239082 A1 10/2007 Schultheiss et al.
2007/0239253 A1 10/2007 Jagger et al.
2007/0244423 A1 10/2007 Zumeris et al.
2007/0250052 A1 10/2007 Wham
2007/0255270 A1 11/2007 Carney
2007/0282301 A1 12/2007 Segalescu et al.
2007/0299481 A1 12/2007 Syed et al.
2008/0097251 A1 4/2008 Babaev
2008/0146918 A1* 6/2008 Magnin ................ A61B 8/4461 600/437
2008/0188913 A1 8/2008 Stone et al.
2008/0294037 A1 11/2008 Richter
2009/0041833 A1 2/2009 Bettinger et al.
2009/0227992 A1 9/2009 Nir et al.
2009/0230822 A1 9/2009 Kushculey et al.
2009/0234282 A1 9/2009 McAndrew et al.
2009/0247945 A1 10/2009 Levit et al.
2009/0254114 A1 10/2009 Hirszowicz et al.
2009/0299447 A1 12/2009 Jensen et al.
2010/0016862 A1 1/2010 Hawkins et al.
2010/0022950 A1 1/2010 Anderson et al.
2010/0036294 A1 2/2010 Mantell et al.
2010/0094209 A1 4/2010 Drasler et al.
2010/0114020 A1 5/2010 Hawkins et al.
2010/0114065 A1 5/2010 Hawkins et al.
2010/0121322 A1 5/2010 Swanson
2010/0125244 A1 5/2010 McAndrew
2010/0179424 A1 7/2010 Warnking et al.
2010/0274189 A1 10/2010 Kurth et al.
2010/0286709 A1 11/2010 Diamant et al.
2010/0305565 A1 12/2010 Truckai et al.
2011/0034832 A1 2/2011 Cioanta et al.
2011/0118634 A1 5/2011 Golan
2011/0208185 A1 8/2011 Diamant et al.
2011/0257523 A1 10/2011 Hastings et al.
2011/0295227 A1 12/2011 Hawkins et al.
2012/0071889 A1 3/2012 Mantell et al.
2012/0095461 A1 4/2012 Herscher et al.
2012/0116289 A1 5/2012 Hawkins et al.
2012/0143177 A1 6/2012 Avitall et al.
2012/0157991 A1 6/2012 Christian
2012/0203255 A1 8/2012 Hawkins et al.
2012/0253358 A1 10/2012 Golan et al.
2012/0271339 A1 10/2012 O'beirne et al.
2012/0289889 A1 11/2012 Genstler et al.
2013/0030431 A1 1/2013 Adams
2013/0041355 A1 2/2013 Heeren et al.
2013/0116714 A1 5/2013 Adams et al.
2013/0123694 A1 5/2013 Subramaniyan et al.
2013/0150874 A1 6/2013 Kassab
2013/0253622 A1 9/2013 Hooven
2014/0005576 A1 1/2014 Adams et al.
2014/0039513 A1 2/2014 Hakala et al.
2014/0046229 A1 2/2014 Hawkins et al.
2014/0214061 A1 7/2014 Adams et al.
2014/0277033 A1* 9/2014 Taylor ............ A61B 17/320068 606/169
2014/0350401 A1 11/2014 Sinelnikov
2015/0238209 A1 8/2015 Hawkins et al.
2015/0320432 A1 11/2015 Adams
2016/0135828 A1 5/2016 Hawkins et al.
2016/0151081 A1 6/2016 Adams et al.
2016/0174995 A1 6/2016 Turjman et al.
2016/0184022 A1 6/2016 Grace et al.
2016/0262784 A1 9/2016 Grace et al.
2016/0324534 A1 11/2016 Hawkins et al.
2017/0135709 A1 5/2017 Nguyen et al.
2017/0151415 A1 6/2017 Maeda et al.
2017/0311965 A1 11/2017 Adams
2018/0098779 A1 4/2018 Betelia et al.
2018/0153568 A1 6/2018 Kat-Kuoy
2018/0304053 A1 10/2018 Eggert et al.
2018/0360482 A1 12/2018 Nguyen
2019/0069916 A1 3/2019 Hawkins et al.
2019/0262069 A1* 8/2019 Taff .................... A61B 18/1492
2019/0365400 A1 12/2019 Adams et al.
2020/0085458 A1 3/2020 Nguyen et al.
2020/0297366 A1 9/2020 Nguyen et al.
2021/0085347 A1 3/2021 Phan et al.
2021/0085383 A1 3/2021 Vo et al.
2021/0338258 A1 11/2021 Hawkins et al.

(56) References Cited

U.S. PATENT DOCUMENTS

| | | | |
|---|---|---|---|
| 2022/0015785 | A1 | 1/2022 | Hakala et al. |
| 2022/0183708 | A1 | 6/2022 | Phan et al. |
| 2022/0240958 | A1 | 8/2022 | Nguyen et al. |
| 2023/0043475 | A1 | 2/2023 | Adams |
| 2023/0293197 | A1 | 9/2023 | Nguyen et al. |
| 2023/0310073 | A1 | 10/2023 | Adams et al. |
| 2023/0329731 | A1 | 10/2023 | Hakala et al. |
| 2024/0188975 | A1 | 6/2024 | Nguyen |
| 2025/0152191 | A1 | 5/2025 | Nguyen |
| 2025/0186074 | A1 | 6/2025 | Phan et al. |

FOREIGN PATENT DOCUMENTS

| | | | |
|---|---|---|---|
| CA | 2104414 | A1 | 2/1995 |
| CN | 1204242 | A | 1/1999 |
| CN | 1269708 | A | 10/2000 |
| CN | 1942145 | A | 4/2007 |
| CN | 101043914 | A | 9/2007 |
| CN | 102057422 | A | 5/2011 |
| CN | 102271748 | A | 12/2011 |
| CN | 102355856 | A | 2/2012 |
| CN | 102765785 | A | 11/2012 |
| CN | 103068330 | A | 4/2013 |
| CN | 203564304 | U | 4/2014 |
| CN | 104582621 | A | 4/2015 |
| CN | 104736073 | A | 6/2015 |
| CN | 105188848 | A | 12/2015 |
| CN | 107072666 | A | 8/2017 |
| CN | 109674508 | A | 4/2019 |
| CN | 111067591 | A | 4/2020 |
| DE | 2635635 | A1 | 2/1978 |
| DE | 3038445 | A1 | 5/1982 |
| DE | 202006014285 | U1 | 12/2006 |
| DE | 102015008949 | A1 | 1/2017 |
| EP | 442199 | A2 | 8/1991 |
| EP | 571306 | A1 | 11/1993 |
| EP | 623360 | A1 | 11/1994 |
| EP | 647435 | A1 | 4/1995 |
| EP | 1596746 | A2 | 11/2005 |
| EP | 2253884 | A1 | 11/2010 |
| EP | 2362798 | B1 | 4/2014 |
| EP | 3434209 | A1 | 1/2019 |
| EP | 3473195 | A1 | 4/2019 |
| JP | S60-191353 | U | 12/1985 |
| JP | S61-135648 | A | 6/1986 |
| JP | S62-099210 | U | 6/1987 |
| JP | S62-275446 | A | 11/1987 |
| JP | H03-63059 | A | 3/1991 |
| JP | H06-125915 | A | 5/1994 |
| JP | H07-47135 | A | 2/1995 |
| JP | H08-89511 | A | 4/1996 |
| JP | H10-99444 | A | 4/1998 |
| JP | H10-314177 | A | 12/1998 |
| JP | H10-513379 | A | 12/1998 |
| JP | 2002538932 | A | 11/2002 |
| JP | 2003510159 | A | 3/2003 |
| JP | 2004081374 | A | 3/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007289707 | A | 11/2007 |
| JP | 2007532182 | A | 11/2007 |
| JP | 2008506447 | A | 3/2008 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2014208305 | A | 11/2014 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| JP | 2019521802 | A | 8/2019 |
| JP | 2020524032 | A | 8/2020 |
| JP | 2022501112 | A | 1/2022 |
| JP | 2022544651 | A | 10/2022 |
| JP | 7637671 | B2 | 2/2025 |
| WO | WO-1989011307 | A1 | 11/1989 |
| WO | WO-1992003975 | A1 | 3/1992 |
| WO | WO-1996024297 | A1 | 8/1996 |
| WO | WO-1999000060 | A1 | 1/1999 |
| WO | WO-1999002096 | A1 | 1/1999 |
| WO | WO-2000056237 | A2 | 9/2000 |
| WO | WO-2001024715 | A1 | 4/2001 |
| WO | WO-2004069072 | A2 | 8/2004 |
| WO | WO-2005099594 | A1 | 10/2005 |
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009121017 | A1 | 10/2009 |
| WO | WO-2009126544 | A1 | 10/2009 |
| WO | WO-2009136268 | A1 | 11/2009 |
| WO | WO-2009152352 | A2 | 12/2009 |
| WO | WO-2010014515 | A2 | 2/2010 |
| WO | WO-2010054048 | A3 | 9/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2013169807 | A1 | 11/2013 |
| WO | WO-2014025397 | A1 | 2/2014 |
| WO | WO-2014025620 | A1 | 2/2014 |
| WO | WO-2015017499 | A1 | 2/2015 |
| WO | WO-2016077627 | A1 | 5/2016 |
| WO | WO-2016109739 | A1 | 7/2016 |
| WO | WO-2018022593 | A1 | 2/2018 |
| WO | WO-2018075924 | A1 | 4/2018 |
| WO | WO-2019099218 | A1 | 5/2019 |

OTHER PUBLICATIONS

Abraham et al. (1992). "Effect of Humidity and on the dc Breakdown and Rod-Plane Temperature of Rod-Rod Gaps," IEEE Transactions on Electrical Insulation, 27(2):207-213.

Advisory Action received for U.S. Appl. No. 13/615,107, mailed on Nov. 6, 2015, 3 pages.

Advisory Action Received for U.S. Appl. No. 12/482,995, mailed on Jun. 2, 2014, 3 pages.

Advisory Action Received for U.S. Appl. No. 12/482,995, mailed on Sep. 29, 2011, 2 pages.

Advisory Action Received for U.S. Appl. No. 12/581,295, mailed on Jul. 3, 2014, 3 pages.

Advisory Action Received for U.S. Appl. No. 13/049,199, mailed on Jun. 7, 2012, 3 pages.

Advisory Action received for U.S. Appl. No. 13/267,383, mailed on Jan. 6, 2014, 4 pages.

After Orbital Atherectomy Video (post treatment) Video 2019, 1 page.

Allen et al. (1993). "Dielectric Breakdown in Nonuniform Field Air Gaps: Ranges of Applicability to dc Voltage Measurement," IEEE Transactions on Electrical Insulation, 28(2):183-191.

Allibone et al. (1972). "Influence of Humidity on the Breakdown of Sphere and Rod Gaps Under Impulse Voltages of Short and Long Wavefronts," Proceedings of the Institution of Electrical Engineers, 119(9):1417-1422.

Amendment After Final Action received for U.S. Appl. No. 12/482,995, filed May 16, 2014, 8 pages.

Amendment in Response to Non-Final Office Action received for U.S. Appl. No. 12/482,995, filed Jan. 9, 2014, 9 pages.

Amighi et al., (2005). "Impact of the Rapid-Exchange Versus Over-the-Wire Technique on Procedural Complications of Renal Artery Angioplasty," J Endovasc Ther., 12:233-239.

(56) References Cited

OTHER PUBLICATIONS

Anvari et al. (1973). "Study of a 40 KV Multistage Spark Gap Operated in Air at Atmospheric Pressure," Exhibit 1044, Declaration of Juanita DeLoach, Ph.D., 3 pages.
Armstrong, Ehrin, "Responses to Question 6 by Patent Owner's Declarants Ehrin Armstrong," Jan. 29, 2020, 5 pages.
Armstrong, Ehrin, "Responses to Questions 1-5 by Patent Owner's Declarants Ehrin Armstrong," Jan. 24, 2020, 4 pages.
Athanasoulis, (1980). "Percutaneous Transluminal Angioplasty: General Principles," American journal of Roentgenology, 135:893-900.
Bank of America Merrill Lynch, "A Simple Solution to a Difficult (and Large) Problem—Initiating Coverage of SWAV," Shockwave Medical Inc., Apr. 1, 2019, pp. 1-22.
Becker et al., (1988). "Radiofrequency Balloon Angioplasty," Rationale and Proof of Principle Investigative Radiology, 23(11):810-817.
Before Orbital Aterectomy Video (pre-treatment) Video 2019, 1 page.
Belmouss (2015). "Effect of Electrode Geometry on High Energy Spark Discharges in Air," Purdue University Open Access Theses, 216 pages.
Ben-Dor et al., "Handbook of Shock Waves", Shockwave Medical, Inc. Patent Owner Exhibit 2223, vol. 2, 2001, 824 pages.
Bittl et al., (1993). "Coronary Artery Perforation during Excimer Laser Coronary Angioplasty," Journal of the American College of Cardiology, 21(5):1158-1165.
Bittl et al., (1993). "Publication Information—Coronary Artery Perforation during Excimer Laser Coronary Angioplasty," Journal of the American College of Cardiology, 21(5): 1-6.
Brace et al. (2009). "Pulmonary Thermal Ablation: Comparison of Radiofrequency and Microwave Devices by Using Gross Pathologic and CT Findings in a Swine Model," Radiology, 251(3):705-711.
Brinton et al., (2016). "Publication Information—TCT-777 Safety and Performance of the Shockwave Medical Lithoplasty® System in Treating Calcified Peripheral Vascular Lesions: 6-Month Results from the Two-Phase Disrupt Pad Study," Journal of the American College of Cardiology, 68(18):1-5.
Brinton et al., (2016). "TCT-777 Safety and Performance of the Shockwave Medical Lithoplasty® System in Treating Calcified Peripheral Vascular Lesions: 6-Month Results from the Two-Phase Disrupt Pad Study," Journal of the American College of Cardiology, 68(18):B314.
Brodmann et al., (2018). "Primary outcomes and mechanism of action of intravascular lithotripsy in calcified femoropopliteal lesions: Results of the Disrupt Pad II," Catheter Cardiovasc Interv., 93(2):335-342.
Calcium in the Peripheral and Coronary Arteries: The Pathologist View, Deposition Exhibit from Deposition of Dr. Finn, Mar. 6, 2020, 27 pages.
Canfield et al., (2018). "40 Years of Percutaneous Coronary Intervention: History and Future Directions," Journal of Personalized Medicine, 8(33):1-9.
Cardiology Today's Intervention, "Shockwave Attracts Additional Investment from Abiomed, has IPO," Available Online at <https://www.healio.com/cardiac-vascular-intervention/peripheral/news/online/%7Bf96c1e20-b4a9-4167-bdb8-254e86a8182a%7D/shockwave-attracts-additional-investment-from-abiomed-has-ipo>, Mar. 12, 2019, pp. 1-2.
Chart of Mantell Detailed Mapping of Provisional to '371 Claims Case No. IPR2019-00405 2020, 12 pages.
Cleveland et al. (2000). "Design and Characterization of a Research Electrohydraulic Lithotripter Patterned after the Dornier HM3," Review of Scientific Instruments, 71(6):2514-2525.
Cleveland et al. (2000). "Publication Information—Design and Characterization of a Research Electrohydraulic Lithotripter Patterned after the Dornier HM3," Review of Scientific Instruments, 71, No. 6, 4 pages.
Cleveland et al., (2012). "The Physics of Shock Wave Lithotripsy", Extracorporeal Shock Wave Lithotripsy, Part IV, Chapter 38, pp. 317-332.
Concise Description of Relevance Accompanying Third Party Preissuance Submission Under 37 CFR 1.290 for U.S. Appl. No. 15/817,073, filed Aug. 5, 2019, 31 pages.
Concise Description of Relevance Accompanying Third Party Preissuance Submission Under 37 CFR 1.290 for U.S. Appl. No. 16/028,225, filed Aug. 2, 2019, 4 pages.
Concise Description of Relevance Accompanying Third Party Preissuance Submission Under 37 CFR 1.290 U.S. Appl. No. 16/240,556, filed Sep. 20, 2019, 14 pages.
Connors et al., (2003). "Renal Nerves Mediate Changes in Contralateral Renal Blood Flow after Extracorporeal Shockwave Lithotripsy", Nephron Physiology, vol. 95, pp. 67-75.
Corrected Notice of Allowance received for U.S. Appl. No. 16/544,516, mailed on May 26, 2020, 5 pages.
Das et al., (2014). "Technique Optimization of Orbital Atherectomy in Calcified Peripheral Lesions of the Lower Extremities," Catheterization and Cardiov Interv, 83:115-122.
Deagon (2019). "Technology—Shockwave Medical IPO Soars On First Day Of Trading," Investor's Business Daily, Available Online at <https://www.investors.com/news/technology/shockwave-medical-ipo-soars-trading/>, pp. 1-15.
Decision Instituting Inter Partes Review for U.S. Pat. No. 8,956,371, by the Patent Trial and Appeal Board dated Jul. 9, 2019, 28 pages.
Decision Instituting Inter Partes Review of U.S. Pat. No. 9,642,673, by the Patent Trial and Appeal Board dated Jul. 22, 2019, 22 pages.
Decision of Appeals Notice received for Japanese Patent Application No. 2011-534914, mailed on Oct. 17, 2016, 2 pages of Official Copy only.
Decision to Grant received for European Patent Application No. 13756766.5, mailed on May 27, 2016, 2 pages.
Decision to Grant received for European Patent Application No. 09763640.1, mailed on Feb. 22, 2018, 2 pages.
Decision to Grant received for European Patent Application No. 09825393.3, mailed on Mar. 13, 2014, 2 pages.
Decision to Grant received for European Patent Application No. 13827971.6, mailed on Jan. 31, 2019, 2 pages.
Decision to Grant received for Japanese Patent Application No. 2011-513694, mailed on Oct. 7, 2014, 3 pages.
Declaration and CV of Aloke V. Finn Case IPR2019-00405 Feb. 20, 2020, 45 pages.
Declaration and CV of Jeffrey Chambers Case IPR2019-00405 Dec. 19, 2020, 32 pages.
Declaration of Dr. Morten Olgaard Jensen dated Dec. 6, 2018, pp. 1-137.
Declaration of Juanita DeLoach Exhibit 1236, Case IPR2019-00408 Feb. 18, 2020, 4 pages.
Declaration of Natalie J. Grace dated Apr. 10, 2019, pp. 1-3.
Declaration of Natalie J. Grace, Apr. 22, 2019, pp. 1-5.
Declaration of William Patrick Stephens, Apr. 22, 2019, pp. 1-6.
Deposition Exhibit from Deposition of Dr. Jensen, Balloon Attributes that Impact Deliverability, Mar. 4, 2020, 1 page.
Deposition Exhibit from Deposition of Dr. Jensen, Diagram from Wikipedia Page for Balloon Catheters, Mar. 4, 2020, 1 page.
Deposition Exhibit from Deposition of Dr. Jensen, Figures 1 and 2 of JP Patent No. 62-275446 (color added), Mar. 4, 2020, 1 page.
Deposition Exhibit from Deposition of Dr. Jensen, Handwritten Diagram, Mar. 4, 2020, 1 page.
Deposition Exhibit of Ronald David Berger Case No. IPR2019-00405 Jan. 27, 2020, 42 pages.
Deposition Transcript (compressed) of Dr. Aloke Finn, Case No. IPR2019-00405, Mar. 6, 2020, 31 pages.
Deposition Transcript (compressed) of Dr. Daniel van der Weide, Case No. IPR2019-00409, U.S. Pat. No. 8,728,091 B2, Jan. 10, 2020., 111 pages.
Deposition Transcript (compressed) of Dr. Jeffrey Chambers, Case No. IPR2019-00405, Mar. 2, 2020., 81 pages.
Deposition Transcript (compressed) of Dr. Morten Olgaard Jensen, Case No. IPR2019-00405, U.S. Pat. No. 8,956,371, Mar. 4, 2020, 73 pages.
Deposition Transcript (compressed) of Dr. Morten Olgaard Jensen, Case No. IPR2019-00408, U.S. Pat. No. 9,642,673, Feb. 26, 2020, 80 pages.

(56) References Cited

OTHER PUBLICATIONS

Deposition Transcript (compressed) of Ronald David Berger Case No. IPR2019-00405 Jan. 27, 2020, 103 pages.
Dewhirst et al., (2003). "Basic Principles of Thermal Dosimetry and Thermal Thresholds for Tissue Damage from Hyperthermia International," Journal of Hyperthermia, 19(3):267-294.
Dewhirst et al., (2003). "Publication Information—Basic Principles of Thermal Dosimetry and Thermal Thresholds for Tissue Damage from Hyperthermia," International Journal of Hyperthermia, 19(3):1-3.
Diamondback 360® Peripheral Orbital Atherectomy System, Cardiovascular Systems, Inc., Patent Owner Exhibit 2231, 2019, 58 pages.
Dictionary.com Definition of 'Angioplasty' Available Online at <https://www.dictionary.com/browse/angioplasty>, pp. 1-5.
Dodd, (1842). "Two Cases of Calculus in the Bladder, in Which Lithotripsy Was Performed," Provincial Medical & Surgical Journal, 3(71):368-370.
Dodge Jr., et al., (1992). "Lumen Diameter of Normal Human Coronary Arteries," Influence of Age, Sex, Anatomic Variation, and Left Ventricular Hypertrophy or Dilation Circulation, 86(1):232-246.
Drilling Research on the Electrical Detonation and Subsequent Cavitation in a Liquid Technique (Spark Drilling), Drilling Research Division—5718, Sandia Laboratories, Status Report Jul. 1-Dec. 31, 1975, 53 pages.
E-mail from Cook Alciati to Mark Nelson confirming Dr. Chamber's total compensation amount from *Cardiovascular Systems, Inc, CSI* v. *Shockwave*—Dr. Chambers Testimony, Mar. 20, 2020, 1 page.
Extended European Search Report (includes Supplementary European Search Report and Search Opinion) received for European Patent Application No. 09763640.1, mailed on Oct. 10, 2013, 5 pages.
Extended European Search Report and Search Opinion received for European Patent Application No. 09825393.3, mailed on Feb. 28, 2013, 6 pages.
Extended European Search Report received for European Patent Application No. 13827971.6, mailed on Apr. 12, 2016, 8 pages.
Extended European Search Report received for European Patent Application No. 21191690.3, mailed on Jan. 17, 2022, 3 pages.
Farb et al., (2002). "Morphological Predictors of Restenosis After Coronary Stenting in Humans," Circulation, pp. 2974-2980.
FDA Clears Lithoplasty Balloon That Shatters Calcified Lesions With Ultrasound, Diagnostic and Interventional Cardiology, Available Online at <https://www.dicardiology.com/product/fda-clearslithoplasty-balloon-shatters-calcified-lesions-ultrasound>, Sep. 16, 2016, pp. 1-5.
Fernandes et al., (2007). "Enhanced infarct border zone function and altered mechanical activation predict inducibility of monomorphic ventricular tachycardia in patients with ischemic cardiomyopathy," Radiology, 245(3):712-719.
File History for U.S. Pat. No. 9,642,673, May 9, 2017, pp. 1-1789.
File History of U.S. Pat. No. 8,956,371, pp. 1-1561.
Final Office Action received for U.S. Appl. No. 12/482,995, mailed on Jul. 22, 2011, 14 pages.
Final Office Action received for U.S. Appl. No. 12/501,619, mailed on Feb. 21, 2012, 12 pages.
Final Office Action received for U.S. Appl. No. 12/611,997, mailed on Dec. 11, 2012, 9 pages.
Final Office Action received for U.S. Appl. No. 12/611,997, mailed on Nov. 10, 2011, 15 pages.
Final Office Action received for U.S. Appl. No. 13/049,199, mailed on Apr. 4, 2012, 10 pages.
Final Office Action received for U.S. Appl. No. 13/207,381, mailed on Nov. 2, 2012, 7 pages.
Final Office Action received for U.S. Appl. No. 14/271,342 mailed on Feb. 27, 2015, 7 pages.
Final Office Action received for U.S. Appl. No. 12/482,995, mailed on Feb. 20, 2014, 11 pages.
Final Office Action received for U.S. Appl. No. 12/581,295, mailed on Jun. 5, 2014, 14 pages.
Final Office Action received for U.S. Appl. No. 12/611,997, mailed on Oct. 24, 2013, 10 pages.
Final Office Action received for U.S. Appl. No. 13/049,199 mailed on Aug. 11, 2014, 8 pages.
Final Office Action received for U.S. Appl. No. 13/207,381, mailed on Nov. 7, 2013, 7 pages.
Final Office Action Received for U.S. Appl. No. 13/267,383, mailed on May 28, 2015, 12 pages.
Final Office Action received for U.S. Appl. No. 13/267,383, mailed on Oct. 25, 2013, 8 pages.
Final Office Action received for U.S. Appl. No. 13/534,658, mailed on Aug. 23, 2016, 11 pages.
Final Office Action received for U.S. Appl. No. 13/615,107 mailed on Sep. 1, 2015, 9 pages.
Final Office Action received for U.S. Appl. No. 13/646,570, mailed on Dec. 23, 2014, 10 pages.
Final Office Action received for U.S. Appl. No. 14/229,735, mailed on Aug. 27, 2015, 7 pages.
Final Office Action received for U.S. Appl. No. 14/273,063, mailed on Dec. 28, 2016, 11 pages.
Final Office Action received for U.S. Appl. No. 15/213,105, mailed on May 4, 2018, 8 pages.
Final Office Action received for U.S. Appl. No. 15/346,132, mailed on Jun. 5, 2019, 12 pages.
Final Office Action received for U.S. Appl. No. 15/979,182, mailed on Oct. 21, 2019, 6 pages.
Final Office Action received for U.S. Appl. No. 16/183,438, mailed on Aug. 11, 2020, 12 pages.
Final Office Action received for U.S. Appl. No. 14/660,539, mailed on Aug. 3, 2017, 11 pages.
Final Written Decision *Ariosa Diagnostics Inc.* vs. *Illumina Inc.* dated Jan. 7, 2016, pp. 1-18.
Final Written Decision for U.S. Pat. No. 8,956,371, by the Patent Trial and Appeal Board dated Jul. 8, 2020, 89 pages.
Fung (1993). "Biomechanics—Mechanical Properties of Living Tissues," Second Edition, Springer, 14 pages.
Gambihler et al., (1994). "Permeabilization of the Plasma Membrane of LI210 Mouse Leukemia Cells Using Lithotripter Shock Waves," The Journal of Membrane Biology, 141:267-275.
Goryachev et al., (1997). "Mechanism of Electrode Erosion in Pulsed Discharges in Water with a Pulse Energy of ~1 J," Tech. Phys. Lett. vol. 23(5):386-387.
Gottlieb (2018). "U.S. Department of Health and Human Services, Food and Drug Administration Report to Congress by Scott Gottlieb," Exhibit 1217, 10 pages.
Grassi et al., (2012). "Novel Antihypertensive Therapies: Renal Sympathetic Nerve Ablation and Carotid Baroreceptor Stimulation," Curr Hypertens Rep, 14:567-572.
Grocela et al., (1997). "Intracorporeal Lithotripsy," Instrumentation and Development Urologic Clinics of North America, 24(1):13-23.
Hawkins et al. U.S. Appl. No. 61/061,170, filed Jun. 13, 2008, titled "Shockwave Balloon Catheter System". pp. 1-50.
Hill (2019). "Deposition Transcript (compressed) of Jonathan M. Hill, M.d.," Exhibit 1211, Case No. IPR2019-00408, U.S. Pat. No. 9,642,673, 63 pages.
Hodges et al., (1994). "Publication Information—Ultrasound Determination of Total Arterial Wall Thickness," Journal of Vascular Surgery, 19(4):1-13.
Hodges et al., (1994). "Ultrasound Determination of Total Arterial Wall Thickness," Journal of Vascular Surgery, 19(4):745-753.
Huang et al., (1998). "Cost Effectiveness of Electrohydraulic Lithotripsy v Candela Pulsed-Dye Laser in Management of the Distal Ureteral Stone," Journal of Endourology, 12(3):237-240.
Intention to Grant received for European Patent Application No. 09763640.1, mailed on Oct. 11, 2017, 8 pages.
Intention to Grant received for European Patent Application No. 13756766.5, mailed on Jan. 8, 2016, 5 pages.
Intention to Grant received for European Patent Application No. 13827971.6, mailed on Sep. 28, 2018, 8 pages.

(56) References Cited

OTHER PUBLICATIONS

International Preliminary Report on Patentability received for PCT Patent Application No. PCT/US2009/047070, mailed on Dec. 23, 2010, 7 pages.
International Preliminary Report on Patentability received for PCT Patent Application No. PCT/US2009/063354, mailed on May 19, 2011, 6 pages.
International Preliminary Report on Patentability received for PCT Patent Application No. PCT/US2011/047070, mailed on Feb. 21, 2013, 7 pages.
International Preliminary Report on Patentability received for PCT Patent Application No. PCT/US2012/023172, mailed on Aug. 15, 2013, 6 pages.
International Preliminary Report on Patentability received for PCT Patent Application No. PCT/US2012/063925, mailed on May 22, 2014, 12 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987 issued on Nov. 20, 2014, 11 pages.
International Preliminary Report on Patentability received for PCT Patent Application No. PCT/US2013/048277 mailed on Jan. 8, 2015, 9 pages.
International Preliminary Report on Patentability received for PCT Patent Application No. PCT/US2013/054104 mailed on Feb. 19, 2015, 8 pages.
International Preliminary Report on Patentability received for PCT Patent Application No. PCT/US2013/055431, mailed on Feb. 26, 2015, 7 pages.
International Preliminary Report on Patentability received for PCT Patent Application No. PCT/US2013/059533 mailed on Mar. 26, 2015, 10 pages.
International Preliminary Report on Patentability received for PCT Patent Application No. PCT/US2015/029088, mailed on Nov. 17, 2016, 8 pages.
International Preliminary Report on Patentability received for PCT Patent Application No. PCT/US2016/060817, mailed on May 31, 2018, 9 pages.
International Preliminary Report on Patentability received for PCT Patent Application No. PCT/US2018/059083, mailed on May 28, 2020, 7 pages.
International Search Report and Written Opinion Received for PCT Application No. PCT/US2018/034855, mailed on Aug. 23, 2018, 13 pages.
International Search Report and Written Opinion Received for PCT Application No. PCT/US2018/059083, mailed on Jan. 22, 2019, 10 pages.
International Search Report and Written Opinion received for PCT Patent Application No. PCT/US2013/031805 mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
International Search Report and Written Opinion received for PCT Patent Application No. PCT/US2015/029088 mailed on Jul. 16, 2015, 13 pages.
International Search Report and Written Opinion received for PCT Patent Application No. PCT/US2015/060453, mailed on Jan. 21, 2016, 15 pages.
International Search Report and Written Opinion received for PCT Patent Application No. PCT/US2016/060817, mailed on Feb. 20, 2017, 13 pages.
International Search Report and Written Opinion received for PCT Patent Application No. PCT/US2020/046134, mailed on Oct. 26, 2020, 18 pages.
International Search Report and Written Opinion received for PCT Patent Application No. PCT/US2020/050899 mailed on Feb. 2, 2021, 19 pages.
International Search Report received for PCT Patent Application No. PCT/US2009/047070, mailed on Jan. 19, 2010, 4 pages.
International Search Report received for PCT Patent Application No. PCT/US2009/063354, mailed on Jun. 11, 2010, 3 pages.
International Search Report received for PCT Patent Application No. PCT/US2012/023172, mailed on Sep. 28, 2012, 3 pages.
International Search Report received for PCT Patent Application No. PCT/US2021/062666 mailed on Mar. 25, 2022, 9 pages.
International Written Opinion received for PCT Patent Application No. PCT/US2009/063354, mailed on Jun. 11, 2010, 4 pages.
International Written Opinion received for PCT Patent Application No. PCT/US2011/047070, mailed on May 1, 2012, 5 pages.
International Written Opinion received for PCT Patent Application No. PCT/US2012/023172, mailed on Sep. 28, 2012, 4 pages.
International Written Opinion received for PCT Patent Application No. PCT/US2009/047070, mailed on Jan. 19, 2010, 5 pages.
Invitation to Pay Additional Fees for PCT Patent Application No. PCT/US2020/050899, mailed on Nov. 5, 2020, 16 pages.
Jacob (1993). "Applications and Design with Analog Integrated Circuits," Second Edition, Prentice-Hall International Editions, pp. 1-8.
Jahnke et al. (2008). "Retrospective Study of Rapid-Exchange Monorail Versus Over-the-Wire Technique for Femoropopliteal Angioplasty," Cardiovascular and Interventional Radiology, vol. 31, pp. 854-859.
Johnson et al. (1992). "Electric Circuit Analysis—Second Edition," Prentice-Hall International Editions, pp. 1-17.
Johnston et al., (2004). "Publication Information—Non-Newtonian Blood Flow in Human Right Coronary Arteries: Steady State Simulations," Journal of Biomechanics, 37(5):1-2.
Johnston et al., (2006). "Non-Newtonian Blood Flow in Human Right Coronary Arteries: Transient Simulations," Journal of Biomechanics, 39(6):1-35.
Kaplan et al., (1993). "Healing after Arterial Dilatation with Radiofrequency Thermal and Nonthermal Balloon Angioplasty Systems," Journal of Investigative Surgery, 6:33-52.
Kini et al., (2015). "Optical Coherence Tomography Assessment of the Mechanistic Effects of Rotational and Orbital Atherectomy in Severely Calcified Coronary Lesions," Catheterization and Cardiovascular Interventions, 86:1024-1032.
Knuttinen et al., (2014). "Unintended Thermal Injuries from Radiofrequency Ablation: Organ Protection with An Angioplasty Balloon Catheter in an Animal Model," Journal of Clinical Imaging Science, 4(1):1-6.
Laeseke et al. (2006). "Multiple-Electrode RF Ablation Creates Confluent Areas of Necrosis: Results in in vivo Porcine Liver," Radiology, 241(1):116-124.
Lauer et al., (1997). "Shock wave permeabilization as a new gene transfer method," Gene Therapy, 4:710-715.
Lee et al., (2017). "Orbital atherectomy for treating de novo, severely calcified coronary lesions: 3-year results of the pivotal ORBIT II trial," Cardiovascular Revascularization Medicine, 18:261-264.
Lee et al., (2018). "Acute Procedural Outcomes of Orbital Atherectomy for the Treatment of Profunda Femoris Artery Disease: Subanalysis of the CONFIRM Registries," J Invasive Cardio, 330(5):177-181.
Lipowski, et al. U.S. Appl. No. 61/051,262 pp. 1-36.
Liu et al., (2015). "Current Understanding of Coronary Artery Calcification," Journal of Geriatric Cardiology, 12:668-675.
Llewellyn-Jones (1963). "The Mechanism of Electrode Erosion in Electrical Discharges," Platinum Metals Rev. vol. 7(2):58-65.
Loske (2007). "Shock Wave Physics for Urologists," Universidad Nacional Autónoma de México, pp. 1-188.

(56) References Cited

OTHER PUBLICATIONS

Med Device Online Angioplasty Balloons Advanced Polymers Inc., Available Online at <https://www.meddeviceonline.com/doc/angioplasty-balloons-0001>, 1 page.
MedlinePlus Angioplasty U.S. National Library of Medicine, Available Online at <https://medlineplus.gov/angioplasty.html>, pp. 1-4.
Millman et al. (1987). "Microelectronics—Second Edition," McGraw-Hill International Editions, pp. 1-15.
Mills et al., (2019). "Cracking the Code on Calcium; Initiate with BUY, $39 Target Canaccord Genuity—Capital Markets," US Equity Research Apr. 1, 2019, pp. 1-63.
Mitomo (2018). "Intravascular lithotripsy: A Novel Technology for Treating Calcified Coronary Stenoses," Cardiovascular News, Online Available at <https://cardiovascularnews.com/intravascular-lithotripsy-anovel-technology-for-treating-calcified-coronary-stenoses>, pp. 1-4.
Mooney et al., (1990). "Monorail Piccolino Catheter: A New Rapid Exchange/Ultralow Profile Coronary Angioplasty System," Catheterization and Cardiovascular Diagnosis, 20:114-119.
Mori et al., "Coronary Artery Calcification and its Progression—What Does it Really Mean", American College of Cardiology Foundation, vol. 11, No. 1, 2018, 16 pages.
Myler et al., (1987). "Recurrence After Coronary Aangioplasty," Catheterization and Cardiovascular Diagnosis, 13:77-86.
Nichols et al., (2005). "McDonald's Blood Flow in Arteries: Theoretical," Experimental and Clinical Principles 5th Edition, pp. 1-9.
Nisonson et al., (1986). "Ambulatory Extracorporeal Shockwave Lithotripsy," Urology, 28(5):381-384.
Non Final Office Action received for U.S. Appl. No. 12/482,995, mailed on Aug. 13, 2014, 10 pages.
Non Final Office Action received for U.S. Appl. No. 12/482,995, mailed on Jul. 12, 2013, 11 pages.
Non Final Office Action received for U.S. Appl. No. 12/611,997, mailed on Nov. 26, 2014, 8 pages.
Non Final Office Action received for U.S. Appl. No. 13/207,381, mailed on Nov. 25, 2014, 5 pages.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non Final Office Action received for U.S. Appl. No. 14/079,463, mailed on Mar. 4, 2014, 9 pages.
Non Final Office Action received for U.S. Appl. No. 12/482,995, mailed on Feb. 11, 2011, 27 pages.
Non Final Office Action received for U.S. Appl. No. 12/501,619, mailed on Nov. 3, 2011, 10 pages.
Non Final Office Action received for U.S. Appl. No. 12/611,997, mailed on Apr. 8, 2013, 9 pages.
Non Final Office Action received for U.S. Appl. No. 12/611,997, mailed on Aug. 24, 2012, 11 pages.
Non Final Office Action received for U.S. Appl. No. 12/611,997, mailed on Jun. 21, 2011, 13 pages.
Non Final Office Action received for U.S. Appl. No. 13/049,199, mailed on Dec. 12, 2011, 10 pages.
Non Final Office Action received for U.S. Appl. No. 13/207,381, mailed on Feb. 22, 2013, 7 pages.
Non Final Office Action received for U.S. Appl. No. 13/207,381, mailed on Jun. 12, 2012, 6 pages.
Non Final Office Action received for U.S. Appl. No. 13/534,658, mailed on Mar. 11, 2016, 12 pages.
Non Final Office Action received for U.S. Appl. No. 14/218,858, mailed on Mar. 30, 2016, 13 pages.
Non Final Office Action received for U.S. Appl. No. 14/515,130, mailed on Jan. 14, 2016, 16 pages.
Non-Final Office Action received for U.S. Appl. No. 12/501,619, mailed on Jan. 28, 2014, 10 pages.
Non-Final Office Action received for U.S. Appl. No. 12/581,295, mailed on Jan. 15, 2015, 14 pages.
Non-Final Office Action received for U.S. Appl. No. 12/581,295, mailed on Mar. 10, 2014, 11 pages.
Non-Final Office Action received for U.S. Appl. No. 12/611,997, mailed on Feb. 13, 2014, 9 pages.
Non-Final Office Action received for U.S. Appl. No. 13/049,199, mailed on Feb. 4, 2014, 8 pages.
Non-Final Office Action received for U.S. Appl. No. 13/207,381, mailed on Feb. 25, 2014, 8 pages.
Non-Final Office Action received for U.S. Appl. No. 13/267,383, mailed on Feb. 25, 2015, 9 pages.
Non-Final Office Action received for U.S. Appl. No. 13/465,264, mailed on Dec. 23, 2014, 13 pages.
Non-Final Office Action received for U.S. Appl. No. 13/615,107, mailed on Apr. 24, 2015, 9 pages.
Non-Final Office Action received for U.S. Appl. No. 13/646,583, mailed on Oct. 31, 2014, 8 pages.
Non-Final Office Action received for U.S. Appl. No. 13/962,315, mailed on Aug. 26, 2015, 20 pages.
Non-Final Office Action received for U.S. Appl. No. 14/061,554, mailed on Mar. 12, 2014, 14 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Non-Final Office Action received for U.S. Appl. No. 14/273,063, mailed on Jun. 3, 2016, 9 pages.
Non-Final Office Action received for U.S. Appl. No. 14/660,539, mailed on Mar. 6, 2017, 14 pages.
Non-Final Office Action received for U.S. Appl. No. 14/660,539, mailed on Nov. 24, 2017, 10 pages.
Non-Final Office Action received for U.S. Appl. No. 14/693,155, mailed on Jan. 15, 2016, 6 pages.
Non-Final Office Action received for U.S. Appl. No. 15/213,105, mailed on Nov. 28, 2017, 7 pages.
Non-Final Office Action received for U.S. Appl. No. 15/346,132, mailed on Dec. 20, 2018, 14 pages.
Non-Final Office Action received for U.S. Appl. No. 15/474,885, mailed on Oct. 5, 2017, 9 pages.
Non-Final Office Action received for U.S. Appl. No. 15/817,073, mailed on Nov. 12, 2019, 18 pages.
Non-Final Office Action received for U.S. Appl. No. 15/979,182, mailed on Aug. 9, 2019, 6 pages.
Non-Final Office Action received for U.S. Appl. No. 16/183,438, mailed on Mar. 31, 2020, 11 pages.
Non-Final Office Action received for U.S. Appl. No. 17/021,905, mailed on Apr. 8, 2022, 11 pages.
Notice of Acceptance Received for Australian Patent Application No. 2009257368, mailed on Aug. 28, 2014, 2 pages.
Notice of Acceptance Received for Australian Patent Application No. 2009313507, mailed on Nov. 17, 2014, 2 pages.
Notice of Acceptance received for Australian Patent Application No. 2013284490, mailed on May 8, 2018, 3 pages.
Notice of Acceptance received for Australian Patent Application No. 2013300176, mailed on Aug. 7, 2017, 3 pages.
Notice of Acceptance received for Australian Patent Application No. 2018204691, mailed on Jun. 18, 2019, 3 pages.
Notice of Allowance received for Canadian Patent Application No. 2,727,429, mailed on May 26, 2015, 1 page.
Notice of Allowance received for Canadian Patent Application No. 2,779,600, mailed on Jul. 7, 2017, 1 page.
Notice of Allowance received for Canadian Patent Application No. 2,881,208, mailed on Oct. 24, 2019, 1 page.
Notice of Allowance received for Chinese Patent Application No. 201380033808.3, mailed on Dec. 29, 2016, 4 pages (Official Copy Only).
Notice of Allowance received for Chinese Patent Application No. 201380041656.1, mailed on Mar. 3, 2017, 4 pages (Official Copy Only).
Notice of Allowance received for Japanese Patent Application No. 2015-036444, mailed on Jan. 13, 2017, 3 pages (Official Copy Only).
Notice of Allowance received for Japanese Patent Application No. 2015-520522, mailed on Feb. 23, 2017, 3 pages (Official Copy Only).

(56) References Cited

OTHER PUBLICATIONS

Notice of Allowance received for Japanese Patent Application No. 2015-526523, mailed on Dec. 4, 2017, 3 pages (Official Copy Only) (See Communication under 37 CFR § 1.98(a) (3)).
Notice of Allowance received for Japanese Patent Application No. 2016-143049, mailed on Nov. 13, 2017, 3 pages (Official copy only).
Notice of Allowance received for Japanese Patent Application No. 2017-212658, mailed on May 13, 2019, 3 pages (Official Copy Only).
Notice of Allowance received for U.S. Appl. No. 14/515,130, mailed on May 2, 2016, 8 pages.
Notice of Allowance received for U.S. Appl. No. 14/515,130, mailed on May 25, 2016, 3 pages.
Notice of Allowance received for U.S. Appl. No. 12/581,295, mailed on Jul. 10, 2015, 15 pages.
Notice of Allowance received for U.S. Appl. No. 12/581,295, mailed on Jul. 29, 2015, 7 pages.
Notice of Allowance received for U.S. Appl. No. 12/611,997, mailed on Apr. 15, 2015, 7 pages.
Notice of Allowance received for U.S. Appl. No. 13/207,381, mailed on Apr. 14, 2015, 7 pages.
Notice of Allowance received for U.S. Appl. No. 13/465,264, mailed on May 8, 2015, 7 pages.
Notice of Allowance received for U.S. Appl. No. 13/957,276, mailed on Aug. 28, 2015, 9 pages.
Notice of Allowance received for U.S. Appl. No. 14/271,276, mailed on Feb. 25, 2015, 8 pages.
Notice of Allowance received for U.S. Appl. No. 12/482,995, mailed on Dec. 24, 2014, 6 pages.
Notice of Allowance received for U.S. Appl. No. 13/049,199, mailed on Dec. 15, 2014, 7 pages.
Notice of Allowance received for U.S. Appl. No. 13/049,199, mailed on Jan. 13, 2015, 4 pages.
Notice of Allowance received for U.S. Appl. No. 13/534,658, mailed on Jan. 5, 2017, 6 pages.
Notice of Allowance received for U.S. Appl. No. 13/534,658, mailed on Jan. 18, 2017, 4 pages.
Notice of Allowance received for U.S. Appl. No. 13/646,570, mailed on Mar. 11, 2015, 7 pages.
Notice of Allowance received for U.S. Appl. No. 13/777,807, mailed on May 19, 2015, 13 pages.
Notice of Allowance received for U.S. Appl. No. 13/831,543, mailed on Oct. 8, 2014, 14 pages.
Notice of Allowance received for U.S. Appl. No. 14/061,554, mailed on Apr. 25, 2014, 8 pages.
Notice of Allowance received for U.S. Appl. No. 14/079,463, mailed on Apr. 1, 2014, 5 pages.
Notice of Allowance received for U.S. Appl. No. 14/218,858, mailed on Aug. 26, 2016, 8 pages.
Notice of Allowance received for U.S. Appl. No. 14/271,342, mailed on Mar. 13, 2015, 5 pages.
Notice of Allowance received for U.S. Appl. No. 14/273,063, mailed on Apr. 12, 2017, 7 pages.
Notice of Allowance received for U.S. Appl. No. 14/660,539, mailed on Apr. 6, 2018, 7 pages.
Notice of Allowance received for U.S. Appl. No. 14/693,155, mailed on Apr. 26, 2016, 9 pages.
Notice of Allowance received for U.S. Appl. No. 15/213,105, mailed on Aug. 10, 2018, 8 pages.
Notice of Allowance received for U.S. Appl. No. 15/220,999, mailed on Oct. 10, 2018, 10 pages.
Notice of Allowance received for U.S. Appl. No. 15/346,132, mailed on Aug. 21, 2019, 8 pages.
Notice of Allowance received for U.S. Appl. No. 15/346,132, mailed on Dec. 17, 2019, 7 pages.
Notice of Allowance received for U.S. Appl. No. 15/474,885, mailed on Feb. 14, 2018, 5 pages.
Notice of Allowance received for U.S. Appl. No. 15/817,073, mailed on Mar. 13, 2020, 8 pages.
Notice of Allowance received for U.S. Appl. No. 16/544,516, mailed on May 5, 2020, 7 pages.
Notice of Allowance received for U.S. Appl. No. 17/185,276, mailed on Jan. 4, 2023, 8 pages.
Notice of Allowance received for U.S. Appl. No. 17/185,276, mailed on Oct. 26, 2022, 10 pages.
Notice of Allowance received for U.S. Appl. No. 13/615,107, mailed on Dec. 31, 2015, 10 pages.
Office Action received for Japanese Patent Application No. 2016-143049, mailed on Jul. 28, 2017, 7 pages (4 pages of English Translation and 3 pages of Official copy).
Office Action received for Australian Patent Application No. 2009257368, issued on Apr. 28, 2014, 4 pages.
Office Action received for Australian Patent Application No. 2009257368, issued on Jul. 31, 2013, 4 pages.
Office Action received for Australian Patent Application No. 2009313507, mailed on Nov. 13, 2013, 3 pages.
Office Action received for Australian Patent Application No. 2013284490, mailed on Jun. 5, 2017, 4 pages.
Office Action received for Australian Patent Application No. 2013284490, mailed on May 3, 2018, 5 pages.
Office Action received for Australian Patent Application No. 2013300176, mailed on Nov. 10, 2016, 2 pages.
Office Action received for Australian Patent Application No. 2018204691, mailed on Jul. 12, 2018, 2 pages.
Office Action received for Canadian Patent Application No. 2,727,429, mailed on Apr. 14, 2015, 4 pages.
Office Action received for Canadian Patent Application No. 2,779,600, mailed on Jan. 4, 2016, 6 pages.
Office Action received for Canadian Patent Application No. 2,877, 160, mailed on Feb. 7, 2019, 4 pages.
Office Action received for Canadian Patent Application No. 2,881,208, mailed on Feb. 12, 2019, 4 pages.
Office Action received for Canadian Patent Application No. 2,779,600, mailed on Oct. 19, 2016, 3 pages.
Office Action received for Chinese Patent Application No. 200980153687.X, mailed on Dec. 26, 2012, 11 pages of Official copy only.
Office Action received for Chinese Patent Application No. 200980153687.X, mailed on Jul. 11, 2013, 11 pages (Official copy only).
Office Action received for Chinese Patent Application No. 201380033808.3, mailed on Jul. 5, 2016, 9 pages (3 pages of English translation and 6 pages of Official copy).
Office Action received for Chinese Patent Application No. 201380041656.1, mailed on Jul. 5, 2016, 9 pages (4 pages of English translation and 5 pages of Official copy).
Office Action received for Chinese Patent Application No. 201380042887.4, mailed on Aug. 8, 2016, 9 pages (4 pages of English translation and 5 pages of Official copy).
Office Action received for Chinese Patent Application No. 201880040835.6, mailed on Oct. 14, 2022, 8 pages.
Office Action received for European Patent Application No. 13735174. 8, mailed on Oct. 15, 2018, 5 pages.
Office Action received for European Patent Application No. 09763640. 1, mailed on Dec. 2, 2016, 4 pages.
Office Action received for Japanese Patent Application No. 2011-513694, mailed on Aug. 27, 2013, 6 pages (3 pages of English Translation and 3 pages of Official copy).
Office Action Received for Japanese Patent Application No. 2011-513694, mailed on Jun. 10, 2014, 4 pages total (2 pages of Official Copy and 2 pages of English Translation).
Office Action Received for Japanese Patent Application No. 2011-534914, mailed on Jan. 13, 2015, 9 pages (7 pages of English Translation and 2 pages of Official Copy.
Office Action received for Japanese Patent Application No. 2011-534914, mailed on Jul. 15, 2014, 3 pages (1 page of English Translation and 2 pages of Official Copy).
Office Action received for Japanese Patent Application No. 2011-534914, mailed on May 10, 2016, 10 pages (4 pages of Official Copy and 6 pages of English Translation).

(56) References Cited

OTHER PUBLICATIONS

Office Action received for Japanese Patent Application No. 2011-534914, mailed on Oct. 1, 2013, 5 pages (2 pages of English Translation and 3 pages of Official copy).
Office Action received for Japanese Patent Application No. 2014-158517, mailed on Feb. 15, 2017, 8 pages (5 pages of English Translation and 3 pages of Official Copy Only).
Office Action Received for Japanese Patent Application No. 2014-158517, mailed on Jun. 22, 2017, 14 pages of official Copy only.
Office Action Received for Japanese Patent Application No. 2014-158517, mailed on May 19, 2015, 5 pages (2 pages of English Translation and 3 pages of Official Copy).
Office Action received for Japanese Patent Application No. 2015-036444, mailed on Feb. 23, 2016, 3 pages of English translation only.
Office Action received for Japanese Patent Application No. 2015-526523, mailed on Jan. 25, 2017, 8 pages (5 pages of English Translation and 3 pages of Official Copy Only).
Office Action received for Japanese Patent Application No. 2016-143049, mailed on Apr. 24, 2017, 5 pages (2 pages of English Translation and 3 pages of Official copy).
Office Action received for Japanese Patent Application No. 2017-212658, mailed on Dec. 20, 2018, 10 pages (6 pages of English Translation and 4 pages of Official Copy).
Office Action received for Japanese Patent Application No. 2017-212658, mailed on Sep. 12, 2018, 8 pages (5 pages of English Translation and 3 pages of Official Copy).
Office Action received for Japanese Patent Application No. 2017-212659, mailed on Jul. 5, 2018, 2 pages (Official Copy Only).
Office Action received for Japanese Patent Application No. 2017-212659, mailed on Mar. 4, 2019, 2 pages (Official Copy Only).
Office Action received for Japanese Patent Application No. 2019-569918, mailed on Feb. 14, 2022, 6 pages. English translation.
Office Action received for Japanese Patent Application No. 2015-036444, mailed on Sep. 14, 2016, 5 pages (3 Pages of English Translation and 2 Pages of Official Copy).
Office Action received for Japanese Patent Application No. 2016-094326, mailed on Dec. 2, 2016, 4 pages (2 pages of English Translation and 2 pages Official Copy Only).
Office Action received for Japanese Patent Application No. 2016-094326, mailed on Jul. 6, 2017, 2 pages (Official Copy Only).
Operator's Manual Intravascular Lithotripsy (IVL) Generator and Connector Cable LBL 61876 Rev. E Mar. 2018, pp. 1-16.
Oral Argument *Cardiovascular Systems Inc.* vs. *Shockwave Medical Inc.* in Inter Partes Review No. IPR2019-00405, dated May 8, 2019, 35 pages.
Otsuka et al., "Has Our Understanding of Calcification in Human Coronary Atherosclerosis Progressed", Coronary Calcification, Apr. 2014, pp. 724-738.
Patent Owner Preliminary Response for U.S. Pat. No. 8,956,371, by the Patent Trial and Appeal Board dated Apr. 10, 2019, 79 pages.
Patent Owner Preliminary Response for U.S. Pat. No. 9,642,673, by the Patent Trial and Appeal Board dated Apr. 24, 2019, 56 pages.
Patent Owner Sur-Reply for U.S. Pat. No. 8,956,371, by the Patent Trial and Appeal Board dated May 24, 2019, 8 pages.
Patent Owner's Response Nov. 7, 2019, 70 pages.
Patent Owner's Response Case No. IPR2019-00409 Nov. 3, 2019, 65 pages.
Patent Owner's Updated Exhibit List for U.S. Pat. No. 8,956,371, by the Patent Trial and Appeal Board dated May 24, 2019, 7 pages.
Patent Owner's Sur-Reply for U.S. Pat. No. 8,956,371, by the Patent Trial and Appeal Board dated Mar. 20, 2020, Mar. 20, 2020, 53 pages.
Patent Owner's Updated Exhibit List for U.S. Pat. No. 8,956,371, by the Patent Trial and Appeal Board dated Mar. 20, 2020, 18 pages.
Patterson et al., (1985). "The Etiology and Treatment of delayed Bleeding following Percutaneous Lithotripsy," The Journal of Urology, 133:447-451.
Peripheral Diamondback 360 Peripheral OAS, Micro Crown, Patents, Cardiovascular Systems, Inc., 2017, 6 pages.
Peripheral Intravascular Lithotripsy (IVL) Catheter—Instructions for Use (IFU) LBL 61932, Rev A Instructions for Use US Jan. 2018, pp. 1-5.
Peripheral Intravascular Lithotripsy (IVL) Catheter Instructions for Use (IFU) LBL 61959, Rev. B Instructions for Use Jun. 2018, pp. 1-7.
Peripheral IVL Case Setup and Execution Shockwave Medical Inc., Available Online at <http://shockwavemedical.com/wp-content/uploads/2018/12/PAD-IVL-Case-Set-Up.pdf>, pp. 1-11.
Petition for Inter Partes Review for U.S. Pat. No. 8,956,371, issued on Feb. 17, 2015, 75 pages.
Petition for Inter Partes Review of U.S. Pat. No. 9,642,673, issued on May 9, 2017, 77 pages.
Petitioner Power of Attorney for U.S. Pat. No. 8,956,371, dated Dec. 6, 2018, pp. 1-2.
Petitioner Power of Attorney for U.S. Pat. No. 9,642,673, dated Dec. 6, 2018, pp. 1-2.
Petitioner's Reply Brief Case IPR2019-00405 Feb. 21, 2020, 65 pages.
Petitioner's Reply Brief, Dated Feb. 18, 2020, 32 pages.
Petitioner's Reply to Patent Owner's Preliminary Response for U.S. Pat. No. 8,956,371, by the Patent Trial and Appeal Board dated May 15, 2019, 7 pages.
Press Release: Shockwave Medical Reports Fourth Quarter and Full Year 2019 Financial Results and Provides Full Year 2020 Financial Outlook, Mar. 4, 2020, 7 pages.
Press Release: St. Francis Participates in Landmark Study Using Sonic Pressure Waves to Treat Heart Blockages, Catholic Health, Jan. 17, 2019, 5 pages.
Publicly Available Professional & Educational Background Summary for Actus Medical, Nov. 2, 2020, 9 pages.
Publicly Available Professional & Educational Background Summary for Alex Asconeguy, Nov. 2, 2020, 4 pages.
Publicly Available Professional & Educational Background Summary for Chris Kunis, 2012, 3 pages.
Publicly available Professional & Educational Background Summary for Clifton Alferness Exhibit 1229 2013, 3 pages.
Publicly available Professional & Educational Background Summary for Daniel Hawkins Exhibit 1226, 2018, 2 pages.
Publicly Available Professional & Educational Background Summary for Doug Hakala, 2016, 5 pages.
Publicly available Professional & Educational Background Summary for Guy Levy Exhibit 1253 2019, 2 pages.
Publicly Available Professional & Educational Background Summary for J. Christopher Flaherty, Nov. 2, 2020, 2 pages.
Publicly available Professional & Educational Background Summary for John Adams Exhibit 1221, 2009, 2 pages.
Publicly available Professional & Educational Background Summary for Krishna Bhatta Exhibit 1251 2005, 2 pages.
Publicly available Professional & Educational Background Summary for Marat Izrailevich Lerner 2020, 3 pages.
Publicly available Professional & Educational Background Summary for Marat Lerner 2008-2020, 4 pages.
Publicly Available Professional & Educational Background Summary for Michael D. Lesh, 2017, 4 pages.
Publicly available Professional & Educational Background Summary for Naoki Uchiyama 2020, 2 pages.
Publicly available Professional & Educational Background Summary for Ralph de la Torre Exhibit 1252 2010, 2 pages.
Publicly Available Professional & Educational Background Summary for Randy Werneth, Nov. 2, 2020, 3 pages.
Publicly available Professional & Educational Background Summary for Robert Mantell Exhibit 1256 2000, 2 pages.
Publicly available Professional & Educational Background Summary for Stepan Khachin 2008-2020, 3 pages.
Publicly Available Professional & Educational Background Summary for Tom Goff, 2017, 3 pages.
Publicly available Professional & Educational Background Summary for Valery Diamant Exhibit 1257 2017, 2 pages.
Redline of Shockwave Provisional to Utility, pp. 1-6.
Response to Final Office Action received for U.S. Appl. No. 12/482,995, filed Sep. 19, 2011, 20 pages.

(56) References Cited

OTHER PUBLICATIONS

Requirement for Restriction/Election received for U.S. Appl. No. 17/021,905 mailed on Nov. 8, 2021, 5 pages.
Ricks (2019). "Long Island Doctors Using Sound Waves to Loosen Calcium Deposits from Arteries, Restore Blood Flow," News/ Health, Available Online at <https://www.newsday.com/news/health/ calcium-treatment-st-francis-hospital-1.27314331>, pp. 1-4.
Rocha-Singh et al. (2014). "Peripheral Arterial Calcification: Prevalence, Mechanism, Detection, and Clinical Implications," Catheterization and Cardiovascular Interventions, vol. 86, pp. E212-E220.
Rosenschein et al., (1992). "Shock-Wave Thrombus Ablation, a New Method for Noninvasive Mechanical Thrombolysis, The American Journal of Cardiology," 70:1358-1361.
Salunke et al., (2001). "Compressive Stress-Relaxation of Human Atherosclerotic Plaque," J Biomed Mater, 55:236-241.
Sasaki et al., (2015). New Insight into Scar-related Ventricular Tachycardia Circuits in Ischemic Cardiomyopathy: Fat Deposition after Myocardial Infarction on Computed Tomography, Heart Rhythm, 12(7):1508-1518.
Schenkman, Noah Ureter Anatomy WebMD LLC, Emedicine. medscape.com, Jul. 10, 2013, 8 pages.
Second Declaration of Natalie J. Grace dated May 24, 2019, pp. 1-2.
Shlofmitz et al., (2019). "Orbital Atherectomy: A Comprehensive Review," Interv Cardiol Clin, 8(2):161-171.
shockwavemedical.com, "Intravascular Lithotripsy (IVL)," Available Online at <https://shockwavemedical.com/technology/intravascular-lithotripsy-ivl/?country=Egypt>, 2019, pp. 1-4.
Simpson et al., (1982). "A New Catheter System for Coronary Angioplasty," The American Journal of Cardiology, 49:1216-1222.
Smith et al., (1992). "Microwave Thermal Balloon Angioplasty in the Normal Rabbit," American Heart Journal, 123(6):1516-1521.
Sokol (2011). "Clinical Anatomy of the Uterus, Fallopian Tubes, and Ovaries," Glob. Libr. Women's Med., pp. 1-12.
Soukas, Peter, "Deposition Transcript (compressed) of Peter Soukas," Cases: IPR2019-00405, IPR2019-00408, IPR2019-00409, Dec. 30, 2019, 81 pages.
Stephens, William, "Deposition Transcript (compressed) of William Patrick Stephens," Case No. IPR2019-00408, Jan. 22, 2020, 55 pages.
Supplemental Declaration of Dr. Morten Olgaard Jensen Case IPR2019-00405 Feb. 21, 2020, 136 pages.
Sweers et al. (2012). "Lightning Strikes: Protection, Inspection, and Repair," Aero Magazine, Quarter 4, pp. 19-28.
Tanaka et al., (2001). "A New Radiofrequency Thermal Balloon Catheter for Pulmonary Vein Isolation," Journal of the American College of Cardiology, 38(7):2079-2086.
Thiem et al., (2018). "The 12-Month Results of the EffPac Trial," Journal of Vascular Surgery, 68(55):e122-e123.
Third Party Preissuance Submission for U.S. Appl. No. 15/817,073, filed Aug. 5, 2019, 3 pages.
Third Party Preissuance Submission for U.S. Appl. No. 15/989,016, filed Mar. 8, 2019, 3 pages.
Third Party Preissuance Submission for U.S. Appl. No. 16/240,556, filed Sep. 20, 2019, 3 pages.
Third-Party Submission Under 37 CFR 1.290 Concise Description of Relevance for U.S. Appl. No. 15/817,073, filed Aug. 5, 2019, 3 pages.
Third-Party Submission Under 37 CFR 1.290 Concise Description of Relevance for U.S. Appl. No. 16/028,225, filed Aug. 2, 2019, 4 pages.
Third-Party Submission Under 37 CFR 1.290 Concise Description of Relevance for U.S. Appl. No. 16/240,556, filed Sep. 20, 2019, 14 pages.
Tomlinson (1991). "Electrical Networks and Filters: Theory and Design," Prentice Hall, pp. 1-9.
Top Cardiovascular Innovation Award Cardiovascular Research Technologies (CRT) 2015, 1 page.
Viljoen (2008). "Flashover Performance of a Rod-Rod Gap Containing a Floating Rod Under Switching Impulses with Critical and Near Critical Times to Crest," A Dissertation Submitted to the Faculty of Engineering and the Built Environment, University of the Witwatersrand, 128 pages.
Vorreuther et al. (1992). "Impact of Voltage and Capacity on the Electrical and Acoustic Output of Intracorporeal Electrohydraulic Lithotripsy," Urological Research, 20(5):355-359.
Vorreuther et al. (1992). "Publication Information—Impact of Voltage and Capacity on the Electrical and Acoustic Output of Intracorporeal Electrohydraulic Lithotripsy," Urological Research, 20, No. 5, Available Online at <https://rd.springer.com/article/10.1007/ BF00922748>): pp. 1-3.
Wagner et al. (1961). "Mechanism of Breakdown of Laboratory Gaps," Transactions of the American Institute of Electrical Engineers. Part III: Power Apparatus and Systems, 80(3):604-618.
Wakerly (1990). "Digital Design: Principles and Practices," Prentice Hall Inc., pp. 1-19.
WebMD.com Definition of 'Angioplasty' Available Online at <https:// www.webmd.com/heart-disease/heart-failure/qa/what-is-the-definition-of-angioplasty> Oct. 29, 2017, pp. 1-2.
Weide, Daniel, "Deposition Transcript (compressed) of Daniel Van Der Weide, Ph.d.," Exhibit 1203, Case No. IPR2019-00408, U.S. Pat. No. 9,642,673 B2, Jan. 13, 2020, 94 pages.
Weide, Daniel, "Exhibit 1116 to Deposition of Daniel Van Der Weide," Jan. 13, 2020, 1 page.
Weide, Daniel, "Exhibit to 1117 Deposition of Daniel Van Der Weide, Ph.d.," Jan. 13, 2020, 1 page.
Weide, Daniel, "Exhibit to 1118 Deposition of Daniel Van Der Weide, Ph.d.," Jan. 13, 2020, 1 page.
Wells Fargo Securities LLC, "SWAV: Initiating With A Market Perform Rating," Shockwave Medical Inc., Apr. 1, 2019, pp. 1-34.
Whitaker (2001). "Modelling of Three-Dimensional Field Around Lightning Rods," University of Tasmania, pp. 1-64.
Whitaker (2001). "Publication Information—Modelling of Three-Dimensional Field Around Lightning Rods," University of Tasmania, 1 page.
Yamamoto et al., (2018). "Effect of orbital atherectomy in calcified coronary artery lesions as assessed by optical coherence tomography," Catheter Cardiovasc Interv, 93(7):1211-1218.
Zhong et al., (1997). "Publication Information—Transient Oscillation of Cavitation Bubbles Near Stone Surface During Electrohydraulic Lithotripsy," Journal of Endourology, 11, 1 page.
Zhong et al., (1997). "Transient Oscillation of Cavitation Bubbles Near Stone Surface During Electrohydraulic Lithotripsy," Journal of Endourology, 11:55-61.
Advisory Action received for U.S. Appl. No. 17/021,905, mailed on Nov. 22, 2022, 4 pages.
Final Office Action received for U.S. Appl. No. 17/021,905, mailed on Sep. 12, 2022, 11 pages.
Extended European Search Report received for European Patent Application No. 24199502.6, mailed on Dec. 13, 2024, 13 pages.
Notice of Allowance and Examiner Interview Summary Record received for U.S. Appl. No. 17/537,325 mailed on Nov. 22, 2024, 11 pages.
Notice of Allowance and Examiner Interview Summary Record received for U.S. Appl. No. 18/582,579 mailed on Oct. 25, 2024, 13 pages.
Notice of Allowance received for Chinese Patent Application No. 202080013l7.6, mailed on Mar. 26, 2025, 4 pages. English translation.
Notice of Allowance received for U.S. Appl. No. 17/021,905 mailed on Feb. 11, 2025, 10 pages.
Office Action received for Australian Patent Application No. 2021396315, mailed on Apr. 4, 2025, 3 pages.
Office Action received for Australian Patent Application No. 2020354360, mailed on Mar. 7, 2025, 3 pages.
Office Action received for Chinese Patent Application No. 20208001317.6, mailed on Jan. 16, 2025, 5 pages. English translation.
Office Action received for Chinese Patent Application No. 202080081317.6 mailed on Jul. 16, 2024, 14 pages. English translation.
Office Action received for European Patent Application No. 21844444.6 mailed on Mar. 24, 2025, 3 pages.

(56) References Cited

OTHER PUBLICATIONS

Office Action received for European Patent Application No. 21844444.6 mailed on Sep. 5, 2024, 5 pages.
Office Action received for Japanese Patent Application No. 2022-518253 mailed on Oct. 10, 2024, 6 pages. English translation.
Office Action received for U.S. Appl. No. 17/021,905 mailed on Mar. 15, 2023, 18 pages.
Office Action received for U.S. Appl. No. 17/537,325 mailed on Apr. 23, 2024, 13 pages.
Requirement for Restriction/Election received for U.S. Appl. No. 18/582,579 mailed on Sep. 5, 2024, 6 pages.
Notice of Acceptance received for Australian Patent Application No. 2020354360, mailed on Feb. 19, 2026, 3 pages.
Notice of Acceptance received for Australian Patent Application No. 2021396315, mailed on Feb. 2, 2026, 3 pages.
Notice of Allowance received for Chinese Patent Application No. 202310535579.0, mailed on Feb. 2, 2026, 6 pages. English translation.
Notice of Allowance received for Japanese Patent Application No. 2024-106084, mailed on Nov. 25, 2025, 4 pages. English translation.
Notice of Allowance received for Japanese Patent Application No. 2023-535464, mailed on Jan. 6, 2026, 4 pages. English translation.
Office Action received for Chinese Patent Application No. 202310535579.0, mailed on Sep. 3, 2025, 8 pages. English translation.
Office Action received for Japanese Patent Application No. 2024-106084 mailed on Aug. 26, 2025, 5 pages. English translation.
Office Action received for Japanese Patent Application No. 2023-535464 mailed on Jul. 14, 2025, 7 pages. English translation.
Office Action received for Indian Patent Application No. 202317042815 mailed on Mar. 10, 2026, 9 pages. English translation.

* cited by examiner

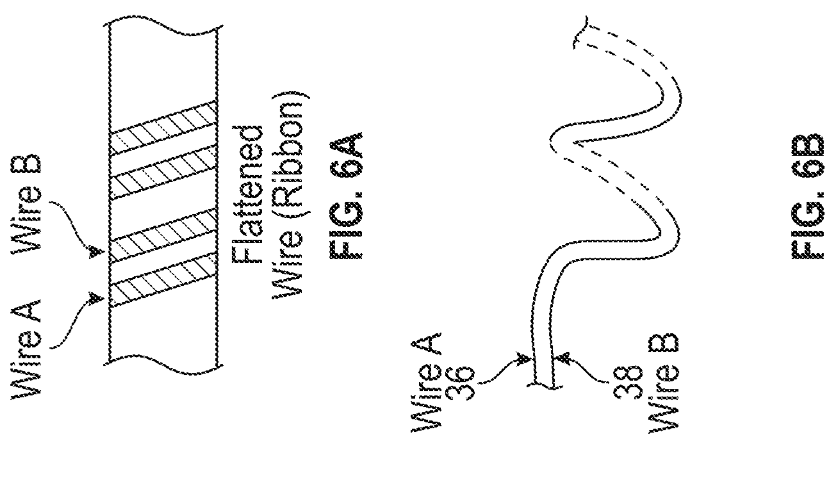
FIG. 6A
FIG. 6B
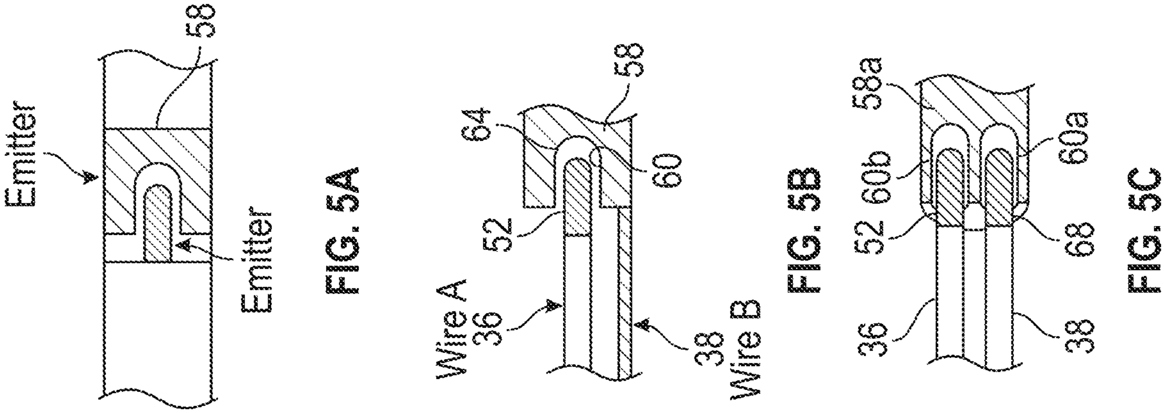
FIG. 5A
FIG. 5B
FIG. 5C
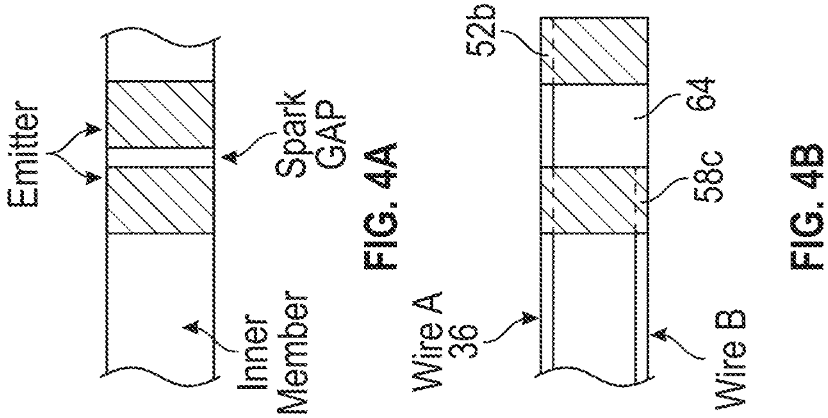
FIG. 4A
FIG. 4B

LESION CROSSING SHOCK WAVE CATHETER

CROSS-REFERENCE TO RELATED APPLICATIONS

The application is a divisional of U.S. patent application Ser. No. 17/021,905, filed on Sep. 15, 2020, which claims priority to U.S. Provisional Patent Application No. 62/904,847, entitled "LESION CROSSING CATHETER WITH LOW PROFILE SHOCK WAVE GENERATOR," filed on Sep. 24, 2019, the content of each of which is hereby incorporated by reference in its entirety.

FIELD OF THE DISCLOSURE

The present disclosure relates generally to catheter devices that can be used to cross a calcified lesion. The catheter includes a distal shock wave generator configured with a very low profile to permit advancement through narrow vascular structures.

BACKGROUND

A wide variety of catheters have been developed to treat arterial disease. For example, treatment systems for percutaneous coronary angioplasty or peripheral angioplasty use angioplasty balloons to dilate a lesion (e.g., a calcified lesion) and restore normal blood flow in an artery. In these types of procedures, a catheter carrying a balloon is advanced into the vasculature along a guidewire until the balloon is aligned with calcified plaques. The balloon is then pressurized to reduce or break the calcified plaques and push them back into the vessel wall. The balloon can have smooth walls or be provided with structures that physically score the lesions in the vessel. Other catheters, known as atherectomy devices, have rotating members for drilling out the lesion.

More recently, catheters have been developed that include one or more electrode pairs positioned inside an angioplasty balloon. In these devices, the catheter is advanced over a guidewire in a patient's vasculature until it is proximal to a lesion. The balloon is inflated with conductive fluid to contact the lesion and then shock wave generators are fired to produce shock waves that direct acoustic waves into the lesion. Shock wave devices are particularly effective for treating calcified lesions because the acoustic waves can crack the lesions without harming the surrounding vasculature. Once the lesions are cracked, the balloon can be expanded further in the vessel to create an improved blood flow lumen.

The shock wave generators are typically electrode pairs excited by the application of high voltage pulses. Efforts have been made to reduce the size of the electrode pairs to allow access to tighter and harder-to-cross calcified lesions. Examples of such low profile designs can be found in U.S. Pat. Nos. 8,747,416 and 10,555,744, and U.S. Publication No. 2019/0150960, all of which are incorporated herein by reference.

While the low profile designs discussed above have been deployed in both coronary and peripheral vessel applications, even those designs have difficulty crossing a partial or total occlusion in vasculature. One approach to deal with the problem is to use guidewire having a shock wave generator at the distal tip. In that case, the catheter proximal and distal shaft portions are reinforced to support the advancement of the guidewire into the occlusion. One or more shock waves are generated to partially open the blockage. The guidewire can then be advanced further into the occlusion where additional shock waves are generated. This sequence can be continued in order to move the guidewire through the occlusion and provide a large enough channel that a balloon catheter can now be inserted. An example of such a shock wave guidewire design can be found in U.S. Pat. No. 9,730,715, incorporated herein by reference.

While placing a shock wave electrode on the tip of a guidewire can lead to an extremely low profile structure, such an approach has some disadvantages compared to low profile designs that include an inflatable balloon. For example, the guidewire necessarily has a soft tip which cannot be easily pushed through a blockage. In addition, the guidewire design is unipolar, with one electrode at the tip of the guidewire and the second electrode defined by a pad affixed to the patient's body. This means that the patient is part of the electrical circuit. In addition, the guidewire design does not have a balloon at the tip. A balloon is advantageous in that it can shield the tissue from direct contact with the plasma that is generated during shock wave creation. A balloon also ensures that the conductive fluid surrounds the electrodes during shock wave generation.

Accordingly, there is a need to provide a catheter design with a lower profile than previous approaches that incorporates an angioplasty balloon and includes a bipolar electrical circuit to generate shockwaves inside a balloon.

BRIEF SUMMARY

The above objects are realized in a catheter for treating occlusions in blood vessels that has at least one electrode pair inside of a flexible angioplasty balloon at the distal end of the catheter. In some designs, the electrodes are coplanar reducing the diameter of the device. In addition, a low profile balloon is used that does need to be folded before insertion into the cardiovascular system. Such a balloon can be expanded a relatively small amount sufficient to immerse the electrodes in a conductive fluid before generating shock waves at the electrodes to treat an occlusion. The balloon can be made of material having elastomeric properties such that it returns to its original low profile configuration when it is deflated following treatment.

The invention provides a catheter for treating occlusions in blood vessels. An exemplary catheter for treating occlusions in blood vessels comprises a tubular guidewire sheath defining a first lumen for receiving a guidewire and a second lumen for carrying a first wire; a shock wave generator located near a distal end of the catheter, said shock wave generator including at least one electrode pair, with electrodes of each pair being spaced apart to define at least one gap; a first wire extending within the second lumen, with a proximal end of the first wire being connectable to a pulsed voltage source and with a distal end of the first wire being connected to the at least one electrode pair; a reinforced sheath wrapped circumferentially around the guidewire sheath, wherein a proximal end of the reinforced sheath is connectable to the pulsed voltage source and a distal end of the reinforced wire sheath is connected to the at least one electrode pair, such that when high voltage pulses are applied across the reinforced wire sheath and the first wire, current flows across the at least one gap creating shock waves for treating an occlusion; and a cap sealably attached to the distal end of the catheter and surrounding the at least one electrode pair, said cap being fillable with a conductive fluid. The cap can be flexible and can be expanded thereby providing space between an inner wall of the cap and the at least one electrode pair.

A second exemplary catheter for treating occlusions in blood vessels comprises a tubular guidewire sheath defining a plurality of lumens, the plurality of lumens comprising a first lumen for carrying a guidewire; a shock wave generator located near a distal end of the catheter, said shock wave generator including at least one distal electrode pair, with electrodes of each pair being spaced apart to define at least one gap; a first wire and a second wire, wherein proximal ends of the first wire and the second wire are connectable to a pulsed voltage source, and wherein distal ends of the first wire and the second wire are connected to the at least one distal electrode pair such that when high voltage pulses are applied across the first wire and the second wire, current flows across the at least one gap creating shock waves for treating an occlusion; and a flexible cap sealably attached to the distal end of the catheter and surrounding the at least one electrode pair, said flexible cap being inflatable with conductive fluid such that the cap expands to provide a space between an inner wall of the cap and the at least one electrode pair.

DESCRIPTION OF THE FIGURES

FIG. 4A illustrates a top view of a ring electrode configuration according to some embodiments of the subject invention FIG. 4B illustrates a magnified side view of the embodiment of FIG. 4A.

FIG. 5A illustrates a top view of a tongue-and-groove electrode configuration according to some embodiments of the subject invention.

FIG. 5B illustrates a side views of the embodiment of FIG. 5A.

FIG. 5C illustrates an exploded view of an alternative tongue-and-groove electrode configuration arranged to produce two electrode pairs, according to some embodiments of the subject invention.

FIG. 6A illustrates a helical electrode configuration according to some embodiments of the subject invention.

FIG. 6B illustrates the helical electrode configuration of FIG. 6A showing just the helically coiled wires.

DETAILED DESCRIPTION

Figure 1A:
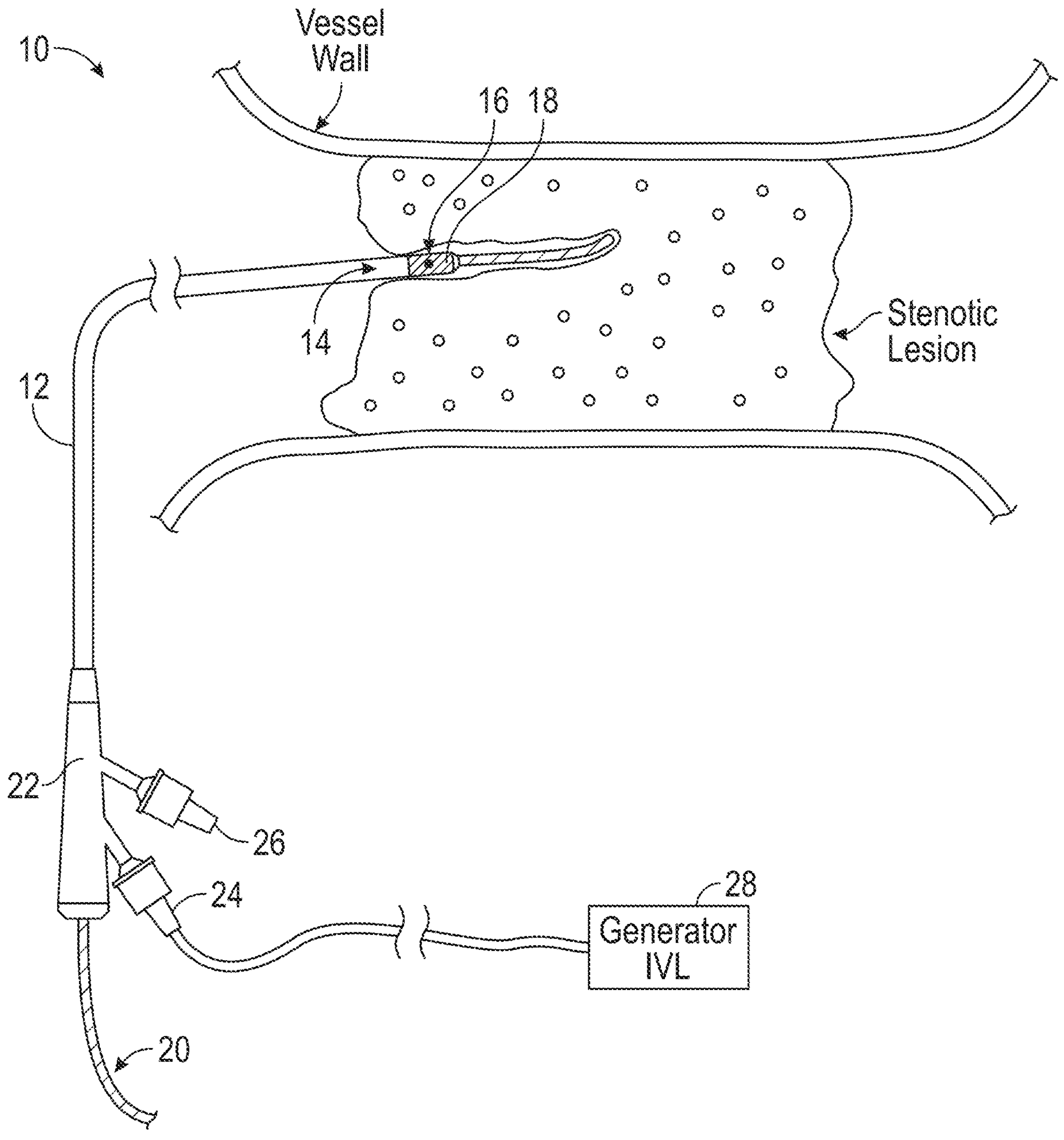
FIG. 1A is an illustration of a shock wave angioplasty catheter being used to treat an occlusion in a blood vessel, according to one embodiment of the subject invention.

The following description is presented to enable a person of ordinary skill in the art to make and use the various embodiments disclosed herein. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but are to be accorded the scope consistent with the claims.

The assignee herein has developed a number of low-profile shock wave electrodes that may be suitable for use in angioplasty and/or valvuloplasty procedures. For example, in U.S. Pub. No. 2019/0150960, the assignee discloses a low-profile electrode assembly, in which an outer electrode is formed by a conductive sheath, and an inner electrode is formed by removing a portion of an insulated wire (e.g., cutting a hole in the insulating layer near the end of the wire) to expose an electrically conductive portion of the insulated wire. The inner electrode is placed a controlled distance apart from the side edge of the conductive sheath to allow for a reproducible arc for a given current and voltage.

More recently, the assignee has developed a number of coplanar electrode assemblies for use in shock wave catheters. These designs provide novel configurations of electrode pairs having, e.g., helical structures and tongue-and-groove designs, with respective electrodes on the same lateral plane to limit the overall thickness of the electrode assemblies. These assemblies are particularly advantageous for generating shock waves in tight, hard-to-pass lesions or totally occluded vasculature. For example, in U.S. Pat. No. 9,993,292 and U.S. Publication No. 2018/0098779, incorporated herein by reference, the assignee discloses forming electrode pairs from helically wound wires to generate shock waves at various gaps positioned circumferentially around a tubular structure. In U.S. Pat. No. 10,555,744, also incorporated herein by reference, the assignee discloses a tongue-and-groove electrode assembly in which electrode pairs are formed from a groove-shaped cut-out in a conductive sheath and a coplanar tongue-shaped protrusion extending into the groove-shaped cut-out.

Described herein are catheters incorporating low-profile design elements that permit intravascular lithotripsy (IVL) treatment in tighter, hard-to-cross calcific lesions and chronic total occlusions. The present invention is similar to existing IVL systems in that it can comprise an array of lithotripsy emitters (e.g., electrode pairs) on a catheter that is entered into a patient's vasculature to deliver shock waves to an occlusion. However, the present invention additionally includes a low-profile angioplasty balloon attached to the distal end of the catheter that can be positioned in a patient's vasculature without folding. When deflated, the surface area of the balloon is small enough that the balloon does not need to be folded while advancing the catheter through a blood vessel. The low profile of the no-fold balloon advantageously allows the catheter to advance into even tighter regions of vasculature, such as those that are partially or totally occluded. Once the balloon has been positioned, the elastomeric material properties of the low-profile balloon allow the balloon to inflate with conductive fluid to increase the balloon's profile, i.e., in order to contact an occlusion and provide space in the balloon for conductive fluid to immerse the electrodes.

In some embodiments, the catheters described herein include additional low-profile elements, such as coplanar electrodes, which further reduce the diameter of the distal end of the catheter. Additionally or alternatively, the catheters may provide an electrical connection to the electrodes by way of a reinforced wire sheath wrapped circumferentially around the catheter shaft. The reinforced wire sheath provides improved kink resistence, torqueability, and pushability to the catheter for more easily maneuvering the device within a patient's vasculature. Including at least one electrical connection integrated into the reinforced wire sheath also improves the low-profile aspects of the device by reducing the number of wires or other conductors that must be carried elsewhere in the catheter.

FIG. 1A illustrates an exemplary catheter 10 for treating occlusions in blood vessels according to an embodiment of the subject invention. The catheter 10 is advanced into an occlusion in a patient's vasculature, such as the stenotic lesion depicted in FIG. 1A, over a guidewire 20 carried in a guidewire sheath. A distal end 14 of the catheter 10 includes a shock wave generator 16 that produces shock waves at a plurality of emitters (e.g., electrode pairs) to break up calcified lesions. As used herein, the plurality of emitters include electrode pairs having first and second electrode separated by a gap, at which shock waves are formed when a current flows across the gap between the electrodes of the pair (i.e., when a voltage is applied across the first and second electrodes). The electrodes pairs are arranged in a low-profile configuration that reduces the diameter of the distal end 14 of the catheter 10 and permits the treatment of tight, hard-to-cross lesions. In some examples, the shock wave generator 16 includes one or more coplanar electrode pairs, or includes one or more electrodes at least partially recessed into the catheter 10.

A flexible cap 18 (e.g., a low-profile flexible angioplasty balloon) is sealably attached to the distal end 14 of the catheter 10, forming an annular channel around the shaft 12 of the catheter. The flexible cap 18 surrounds the shock wave generator 16, such that the shock waves are produced in a closed system defined by the walls of the cap. The cap 18 is filled with a conductive fluid, such as saline. The conductive fluid allows the acoustic shock waves to propagate from the electrode pairs of the shock wave generator 16 through the walls of the cap 18 and then into the target lesion. In some embodiments, the conductive fluid may also contain an x-ray contrast to permit fluoroscopic viewing of the catheter 10 during use. In some embodiments, the cap is rigid and not flexible.

Figures 1B, 1C:
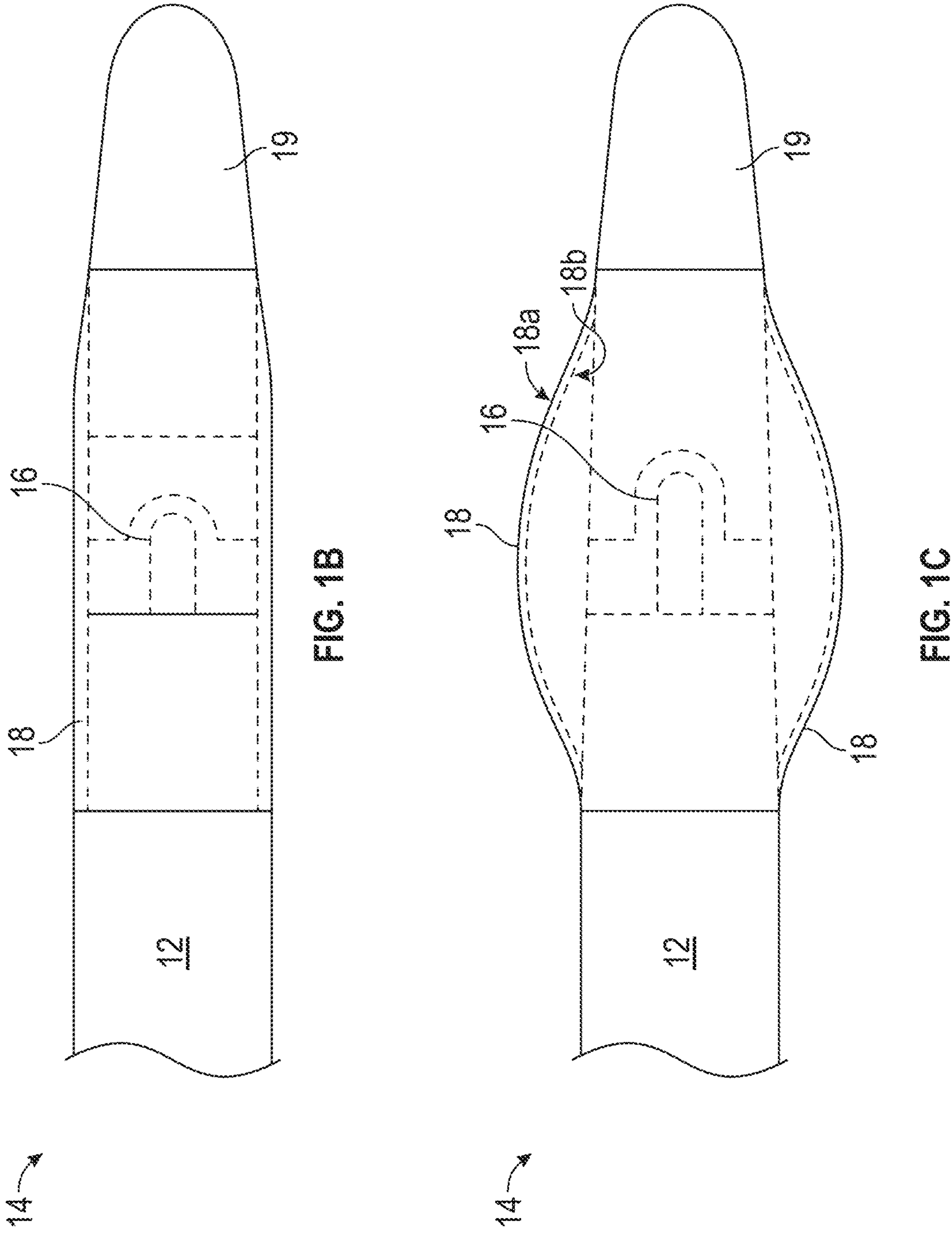
FIG. 1B is an illustration of the distal end of a catheter having a low-profile no-fold balloon in a deflated state in accordance with some embodiments of the subject invention.
FIG. 1C is an illustration of the distal end of the catheter of FIG. 1B showing the low-profile no-fold balloon in an inflated state.

FIGS. 1B-1C provide more detailed views of the distal end 14 of the catheter 10 of FIG. 1A, including an exemplary no-fold angioplasty balloon forming the flexible cap 18 over the shock wave generator 16. The balloon 18 has a small enough diameter and surface area that it does not need to be folded like a conventional angioplasty balloon when advanced through a patient's vasculature. The extremely low profile of the balloon 18 allows the distal end 14 of the catheter to access tightly occluded regions of vasculature. In some examples, the diameter of the catheter's distal end 14 in the region of the balloon 18 is one millimeter or less. To maintain its low profile shape, the balloon 18 is preferably formed of a material having elastomeric properties such that the balloon can be inflated during treatment of an occlusion, and then returns to a low profile state when deflated after treatment. In some examples, the flexible cap 18 is an extruded polymer tube having semi-compliant material properties such that the polymer tube can be inflated and deflated similarly to an angioplasty balloon. As used herein, flexible cap and balloon are used interchangeably to describe the flexible annular structure that surrounds the electrode pairs and is inflated with conductive fluid during treatment.

FIG. 1B shows an exemplary flexible balloon 18 in a deflated state, for instance, during entry, advancing, and positioning of the balloon in a blood vessel. When the balloon 18 is in a deflated state, the surface area of the balloon is small enough that the balloon is not folded when the catheter 10 is advanced through a blood vessel. If the balloon 18 is maneuvered through a patient's blood vessel inside of a guide catheter or some other outer sheath (e.g. a tubular outer jacket of the catheter 10), the surface area of the deflated balloon is small enough that the balloon is not folded inside of the guide catheter or outer jacket. In such examples, the diameter of the balloon is smaller than the diameter of the guide catheter or outer jacket.

Once the balloon 18 has been positioned in a patient's vasculature, additional conductive fluid can be flowed into the balloon to inflate the balloon and gently fix the outer surface of the balloon to a lesion. FIG. 1C shows the same balloon 18 in an inflated state. The balloon 18 is formed of a material having elastomeric properties such that the balloon can accept inflation pressures of between approximately one atmosphere and approximately six atmospheres. The balloon 18 is configured to expand only slightly when inflated with conductive fluid during treatment. For example, the maximum inflated diameter of the balloon 18 may be no more than 10%-15% greater than the original diameter of the balloon (i.e., the diameter of the balloon in a deflated state). The maximum diameter of the balloon in an inflated state can be determined by the material durometer of the balloon 18, its wall thickness, and/or the inflation pressure inside the balloon. When the balloon is inflated with conductive fluid, the balloon 18 expands to provide a space between the inner surface of the balloon and the electrode pairs 16. In some examples, the outer diameter of the guidewire sheath is approximately 0.028 inches and the inner diameter of the inflated balloon 18 is approximately 0.039 inches, providing a space of about 0.011 inches between the guidewire sheath and the inner surface of the balloon. The space ensures that the electrode pairs 16 are immersed in conductive fluid during shock wave generation and that the inner surface of the balloon 18 is sufficiently far from the electrode pairs that the balloon material is not damaged by the shock waves. In some embodiments, the diameter of the inflated balloon 18 is one millimeter or less. Optionally, the outer surface of the balloon 18 includes a hydrophilic coating to facilitate contact between the balloon and the target lesion.

After the lesion has been treated, the balloon 18 can be deflated to its original low profile deflated configuration. When the balloon 18 returns to a deflated state after being inflated, the balloon should return to its original low profile configuration (i.e., a configuration having a small surface area and diameter) such that that the balloon is not folded when removing the catheter 10 from the patient's vasculature.

Returning to FIG. 1A, an exemplary catheter 10 also includes a proximal end or handle 22 that remains outside of a patient's vasculature during treatment. The proximal end 22 includes an entry port for receiving the guidewire 20. The proximal end 22 also includes a fluid port 26 for receiving a conductive fluid for inflating and deflating the flexible cap 18 during treatment. An electrical connection port 24 is also located on the proximal end 22 to provide an electrical connection between the distal shock wave generator 16 and an external pulsed high voltage source 28, such as the intravascular lithotripsy (IVL) generator shown in FIG. 1A.

The catheter 10 also includes a flexible shaft 12 that extends from the proximal handle 22 to the distal end 14 of the catheter. The shaft 12 provides various internal conduits connecting elements of the distal end 14 with the handle 22 of the catheter (see, e.g., FIGS. 2E-2F and FIG. 3E-3F for cross-sections of a region of an example shaft). The shaft 12 includes a guidewire sheath that includes a lumen for receiving the guidewire 20. The guidewire sheath also defines a number of further lumens extending longitudinally through the shaft 12. For instance, one or more wire lumens can be included for carrying conductive wires that electrically connect the pulsed voltage source 28 with electrodes of the distal shock wave generator 16. In some embodiments, one or more fluid lumens (e.g., a fluid inlet lumen and a fluid outlet lumen) are provided in the guidewire sheath for carrying conductive fluid from the fluid port 26 into the cap 18. Optionally, the flexible shaft 12 includes a reinforced wire sheath wrapped circumferentially around the guidewire sheath. The reinforced wire sheath provides mechanical support to the flexible shaft 12 to facilitate torqueing, pushing, and maneuvering of the catheter 10 through a patient's blood vessel. In some embodiments, the reinforced wire sheath is also configured for carrying a current, such that the reinforced wire sheath can be used to connect one or more of the distal electrode pairs of the shock wave generator 16 with the pulsed voltage source 28 (i.e., in lieu of one or more of the conductive wires). In some embodiments, a tubular outer jacket covers the guidewire sheath and the reinforced wire sheath to provide a barrier between active elements of the catheter 10 and the in situ environment.

As shown in FIG. 1A, the catheter 10 can be used to treat occlusions in vasculature, for example, stenotic lesions, calcified portions of an artery, or some other occlusion in a blood vessel. In operation, a physician advances the guidewire 20 from an entry site on a patient (e.g., an artery in the groin area of the leg) to the target region of a vessel (e.g., a region having an occlusion that needs to be broken up). The catheter 10 is then advanced over the guidewire 20 to the target region of the vessel. In some examples, the flexible cap 18 sealed to the distal end 14 is a no-fold balloon having a low profile when deflated, such that the balloon does not need to be folded while the device is advanced through the vasculature. During the positioning stage of treatment, a guide catheter or outer jacket may be used to aid the entry and maneuvering of the catheter 10 within the vasculature. The outer jacket provides tubular linear support to the catheter shaft 12 and retains the deflated state of the flexible cap 18 during pushing, crossing, and placement of the catheter 10. The in situ location of the distal end 14 of the catheter 10 may be determined by x-ray imaging and/or fluoroscopy.

The distal end 14 of the catheter 10 is advanced as far as possible inside the tight lesion. The flexible cap 18 is then inflated by a conductive fluid (e.g., saline and/or saline mixed with an image contrast agent) introduced via the fluid port 26, allowing conductive fluid to expand the cap so that the outer surface of the cap contacts the target lesion. The cap is inflated to IVL pressure, which is between approximately one atmosphere and approximately six atmospheres. The diameter of the flexible cap in an inflated state may be about 10-15% greater than the diameter of the flexible cap in a deflated state. However, in some examples the diameter of the cap in an inflated state is even less than 10% greater than the diameter of the cap in a deflated state. A voltage pulse is then applied by the pulsed high voltage source 28 across one or more electrode pairs (i.e., emitters of the shockwave generator 16). Each pulse initially ionizes the conducive fluid in the flexible cap 18 to create small gas bubbles around the shock wave generator 16 that insulate the electrodes. Fluid can be continuously flowed through the cap 18 during treatment at a constant rate to clear the bubbles and debris from the electrodes. The fluid flow rate may be controlled throughout treatment, but is generally in the range of approximately 1 ml/min to approximately 3 ml/min. At some point, a plasma arc forms across the electrode pairs, creating a low impedance path where current flows freely. The heat from the plasma arc heats the conductive fluid creating a rapidly expanding vapor bubble. The expansion of the vapor bubble creates a shock wave that is conducted through the fluid, through walls of the flexible cap 18, and into an occlusion where the energy breaks up the hardened lesion.

For treatment of an occlusion in a blood vessel, the voltage pulse applied by the voltage pulse generator 28 is typically in the range of approximately 2000 volts to approximately 3000 volts and preferably between 2300 and 3000 volts. The pulse width of the applied voltage pulses ranges between 2 microseconds and 6 microseconds. The repetition rate or frequency of the applied voltage pulses may be between approximately 1 Hz and approximately 10 Hz. However, the preferred voltage and repetition rate may vary depending on, e.g., the size of the lesion, the extent of calcification, the size of the blood vessel, the attributes of the patient, or the stage of treatment. For instance, a physician may start with low energy shock waves and increase the energy as needed during the procedure. The magnitude of the shock waves can be controlled by controlling the voltage, current, duration, and repetition rate of the pulsed voltage from the pulsed voltage source 28. More information about the physics of shock wave generation and their control can be found in U.S. Pat. Nos. 8,956,371; 8,728,091; 9,522,012; and 10,226,265, each of which is incorporated by reference.

During an IVL treatment, one or more cycles of shock waves can be applied to create a more compliant vessel. For example, once the stenosis has been softened sufficiently by a first cycle of shock waves, the flexible cap 18 can be deflated and the distal end 14 of the catheter 10 can be advanced further into the occlusion. The flexible cap 18 is then re-inflated and another cycle of shock waves can be applied. Further advancement of the cap 18 can be attempted after the completion of successive cycles.

The placement and spacing of the electrode pairs can be controlled to provide a more effective shock wave treatment. For instance, the electrode pairs of the shockwave generator 16 may be spaced circumferentially around the distal end 14 of the catheter 10 in consistent increments, e.g., 180 degrees apart or 90 degrees apart, to generate shock waves more evenly around the catheter. In some embodiments, the shock wave generator 16 includes electrode pairs positioned in various groupings spaced longitudinally along the catheter 10 within the flexible cap 18. For example, the shock wave generator 16 may include at least one distal electrode pair and at least one proximal electrode pair. In such examples, the pulsed voltage source 28 can be controlled to selectively generate high voltage pulses at either the proximal or distal electrode pairs, e.g., by applying voltage pulses across differing set of wires or other conductors leading to the respective pairs. In a first stage of treatment (i.e., during initial treatment of the tight or totally-occluding lesion), only the distal electrode pairs are activated to generate shock waves. After the tight lesion has been modified and more proximal portions of the cap 18 are able to cross the lesion, the cap is again inflated and more proximal electrode pairs are activated to generate more proximal shock waves.

The progress of the procedure may be monitored by x-ray and/or fluoroscopy. Shock wave cycles can be repeated until the occlusion has been cleared, or until a channel is formed in the lesion having a diameter sufficient to receive a second treatment device having a larger profile. For example, the enlarged channel can receive a different catheter having a more conventional angioplasty balloon or differently oriented shock wave sources. Catheters of this type are described in U.S. Pat. No. 8,747,416 and U.S. Publication No. 2019/0150960, cited above. Once the lesion has been sufficiently treated, the flexible cap 18 may be inflated further, then deflated, and catheter 10 and guidewire 20 can be withdrawn from the patient.

Figure 1D:
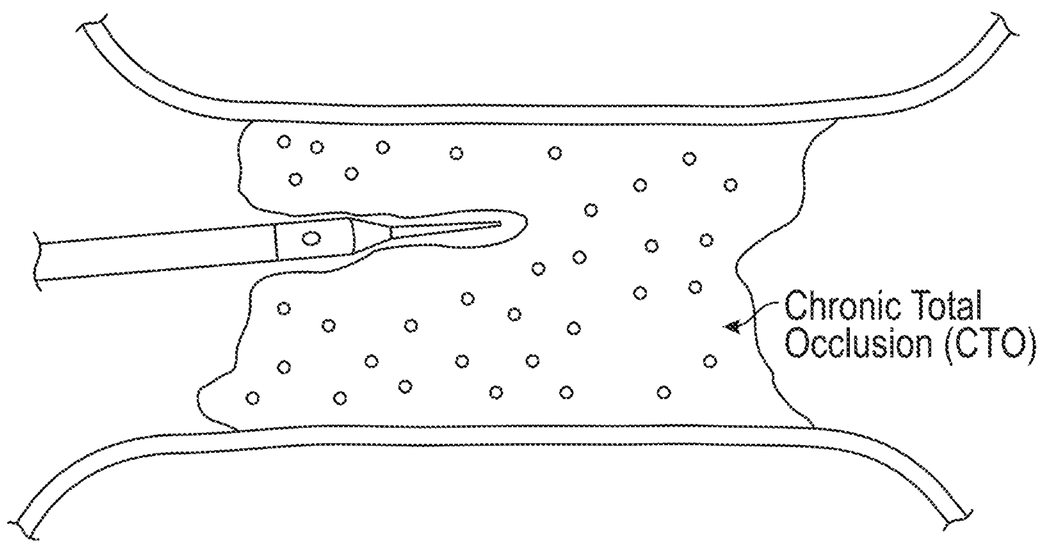
FIG. 1D is an illustration of the catheter of the subject invention being used to treat a chronic total occlusion (CTO).

FIG. 1D depicts the catheter 10 being used to treat a total occlusion in a blood vessel, for instance, a chronic total occlusion (CTO). When treating a total occlusion, the guidewire is advanced at least partially into the stenotic lesion. The catheter is then advanced through the patient's vasculature over the guidewire and at least partially into the lesion. The flexible cap is then inflated with a conductive fluid until the cap gently contacts the lesion. Voltage pulses are then supplied by a pulsed voltage source to electrode pairs at the tip of the catheter to generate shock waves that break up or loosen the lesion. The guidewire and the catheter can then be advanced further into the lesion and the shock wave treatment can be repeated until the total occlusion is cleared or until the diameter of the vessel permits the placement of a larger more conventional angioplasty device.

Figure 1E:
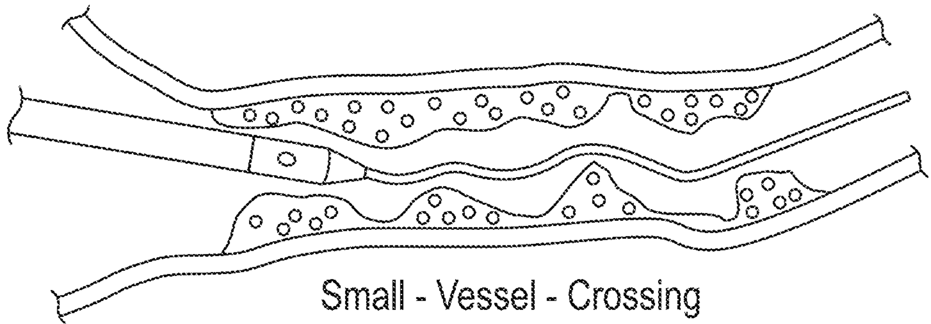
FIG. 1E is an illustration of the catheter of the subject invention being used in a blood vessel highly narrowed by a partial occlusion.

FIG. 1E illustrates the use of the inventive catheter 10 in a small vessel that is partially blocked by a stenotic lesion. In this situation, the guidewire can be advanced much further into the lesion and, in some cases, all the way through the lesion. After positioning the guidewire, the catheter is advanced through the lesion in incremental stages. At each stage, the flexible cap is inflated and shock waves are generated to break up the occlusion and increase the diameter of the blood vessel. As noted above, once the diameter of the vessel is sufficiently large, a larger-diameter catheter may be advanced through the vessel to complete the treatment.

Figure 2A:
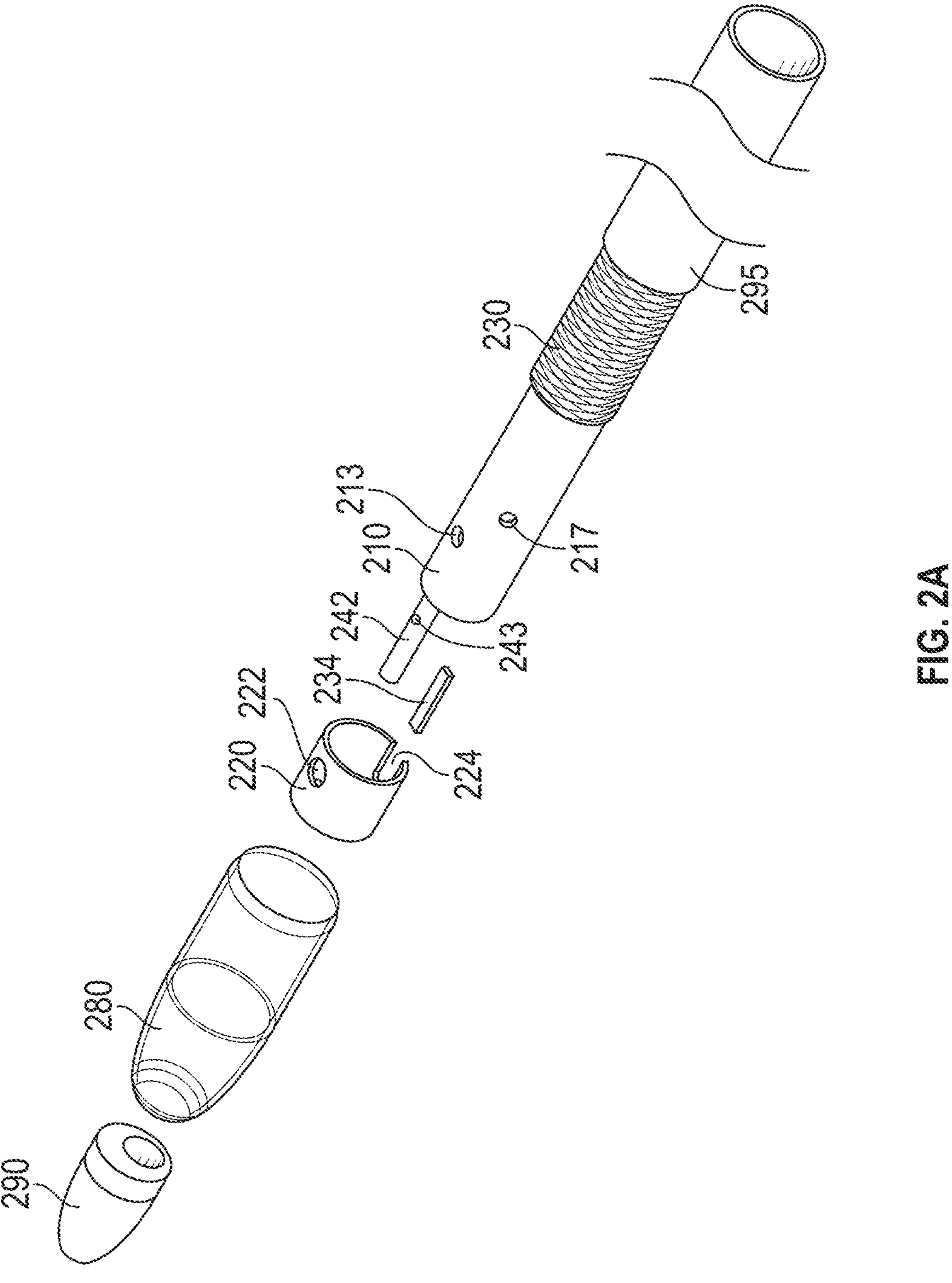
FIG. 2A is an exploded perspective view of a distal section of a catheter according to one embodiment of the subject invention.

FIGS. 2A-2G and 3A-3H provide more detailed views of the distal ends of catheters that can be included in a shock wave angioplasty device, such as any of the catheters of FIGS. 1A-1E and described herein. FIG. 2A illustrates an exploded perspective view of a distal section of an exemplary catheter including two low-profile electrode pairs formed from a conductive sheath (the "emitter band", e.g., a ring electrode) wrapped circumferentially around a guidewire sheath (the "multilumen inner member"). The electrode pairs are electrically connected to an external pulsed voltage source by way of a conductive wire (for example, the polyimide-insulated copper wire) and a conductive reinforced wire sheath (the "flat wire braid") wrapped circumferentially around the guidewire sheath. A cap (e.g., a low-profile angioplasty balloon or a tubular polymer) is sealed to the distal tip of the catheter covering the electrode pairs and a portion of the guidewire sheath. The catheter also includes an outer jacket having a diameter greater than the diameter of the distal section of the catheter. The outer jacket aids the entry and positioning of the catheter by providing circumferential protection and mechanical support to the device.

Figure 2B:
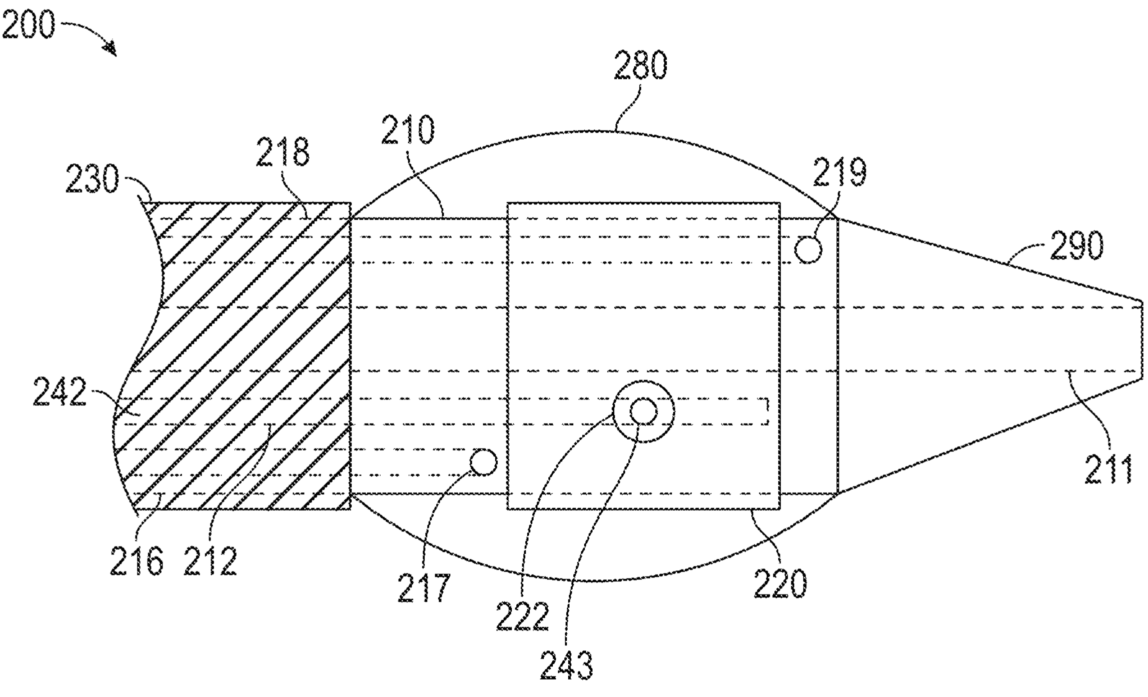
FIG. 2B is a side view illustration of the distal end of the catheter of FIG. 2A, including a first electrode pair and a no-fold balloon over the electrode pair.
Figure 2C:
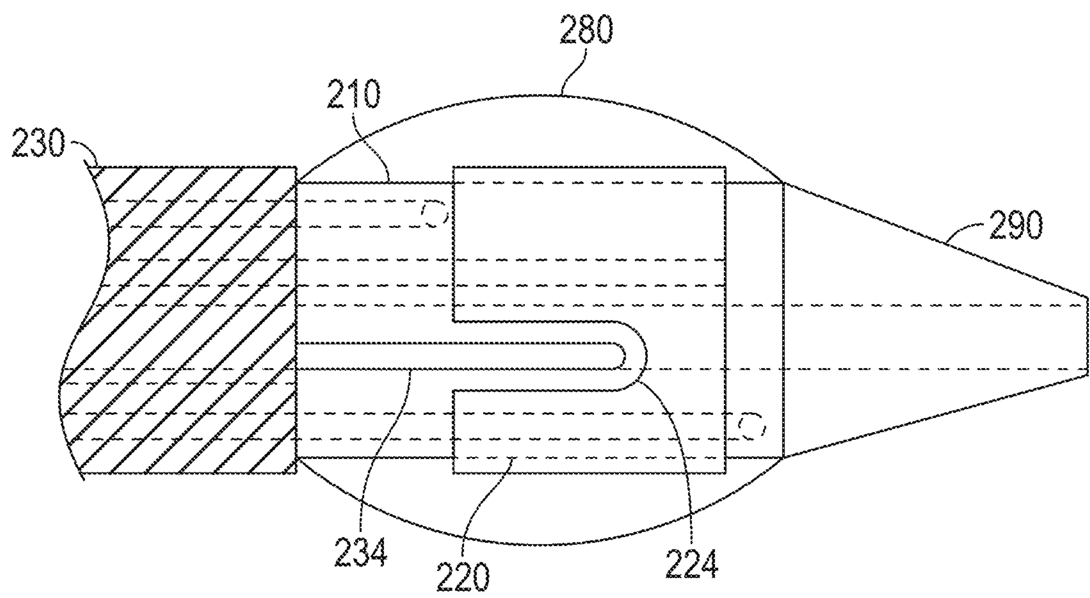
FIG. 2C is an illustration of the embodiment of FIG. 2B rotated by 180 degrees to show a second electrode pair.

FIG. 2B depicts a first side view of the distal end 200 of the exemplary catheter showing a first electrode pair in a dot-circle configuration. FIG. 2C provides a second view of the distal end 200 of the catheter of FIG. 2B rotated by 180 degrees to show a second electrode pair opposite the first electrode pair, the second electrode pair having a tongue-and-groove configuration. As shown in FIGS. 2B-2C, the distal end 200 of the catheter includes a guidewire sheath 210, a shockwave generator including a first electrode pair and a second electrode pair, and a flexible cap 280 surrounding the electrode pairs. The flexible cap 280 is wrapped circumferentially around the guidewire sheath 210 and sealed to the distal end 200 of the catheter using, e.g., an adhesive seal or a thermal bond to form a closed annular channel around a portion of the guidewire sheath 210. In some embodiments, the flexible cap 280 is a no-fold angioplasty balloon (i.e. a low-profile angioplasty balloon) that can be positioned in a patient's vasculature without folding. When the balloon 280 is in a deflated state (see, e.g. FIG. 1B), the surface area of the balloon is small enough that the balloon is not folded when the catheter is advanced into a blood vessel. In some examples, the flexible cap 280 is an extruded tubular structure formed of a semi-compliant polymer material (i.e., an extruded polymer tube). The semi-compliant polymer material allows the flexible cap 280 to inflate slightly responsive to fluid pressure inside the flexible cap, and then return to its original size when under no pressure.

The flexible cap 280 is inflatable with a conductive fluid, for example, saline, such that the cap expands to provide a space between the inner wall of the cap and the electrode pairs (see, e.g., FIG. 1C). In some embodiments, the flexible cap 280 expands a relatively small amount such that the cap retains a low profile (e.g., has a diameter less than 1 millimeter) when it is in an inflated state. For example, the maximum inflated diameter of the flexible cap 280 may be no more than 10%-15% greater than the original diameter of the cap, such that the diameter of the flexible cap in an inflated state is 10-15% greater than the diameter of the cap in a deflated state. However, when inflated, the flexible cap 280 should provide a space sufficient to allow the conductive fluid to surround and immerse the electrode pairs to avoid damage to the cap during shock wave generation. When inflated, the conductive fluid allows the acoustic shock waves from the electrode pairs to propagate through the walls of the cap 280 and into a lesion in contact with the outer surface of the cap. In some embodiments, the conductive fluid also contains an x-ray contrast agent to permit fluoroscopic viewing of the catheter during IVL treatment.

Figure 2D:
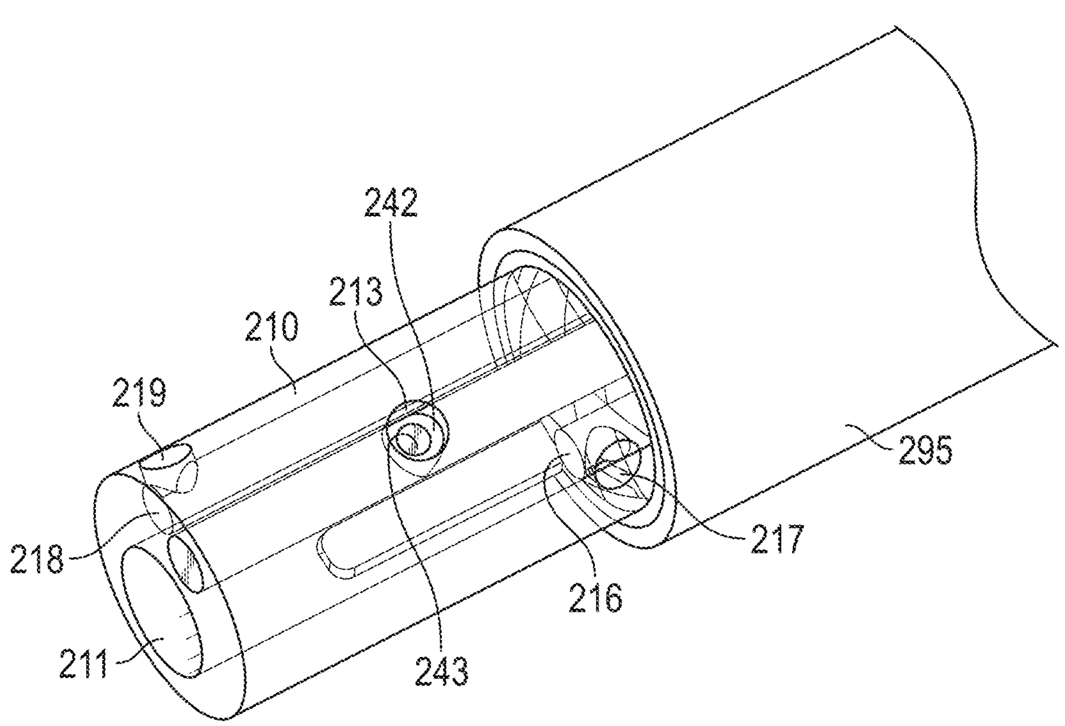
FIG. 2D is an exploded perspective view of an the catheter of FIG. 2A showing a fluid inlet and fluid outlet.

The conductive fluid is admitted into the cap 280 via a fluid inlet 217 in the guidewire sheath 210, and removed from the cap via a fluid outlet 219 in the guidewire sheath. The fluid inlet 217 and fluid outlet 219 provide channels extending from the surface of the guidewire sheath 210 to a respective fluid inlet lumen 216 and fluid outlet lumen 218 in the guidewire sheath (and, more proximally, allow the cap to access fluid supplied by the fluid port shown in FIG. 1A). While treating an occlusion, fluid can be continually flushed through the flexible cap 280 via the inlet 217 and the outlet 219 to clear bubbles and debris produced when high voltage pulses across the electrodes create shock waves in the cap 280. The fluid inlet 217 and fluid outlet 219 are positioned to maximize fluid flow across the electrode pairs, such that fluid flowed through the cap 280 via the inlet and outlet flows across at least one of the electrode pairs. For example, as depicted in FIG. 2B, the fluid inlet 217 and the fluid outlet 219 can be positioned diagonally across the conductive sheath 220, such that one or more of the electrode pairs are positioned between the fluid inlet and the fluid outlet. FIG. 2D provides an exploded perspective view of an IVL catheter embodiment, having a fluid inlet and fluid outlet positioned to flow fluid across an electrode pair.

Figure 2E:
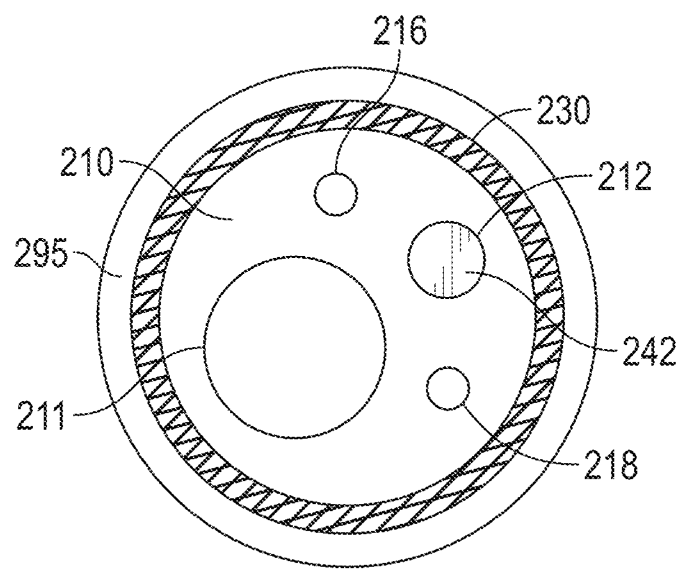
FIG. 2E is a cross-sectional view of the embodiment of FIGS. 2B-2C, taken at a more proximal region of the catheter.
Figure 2F:
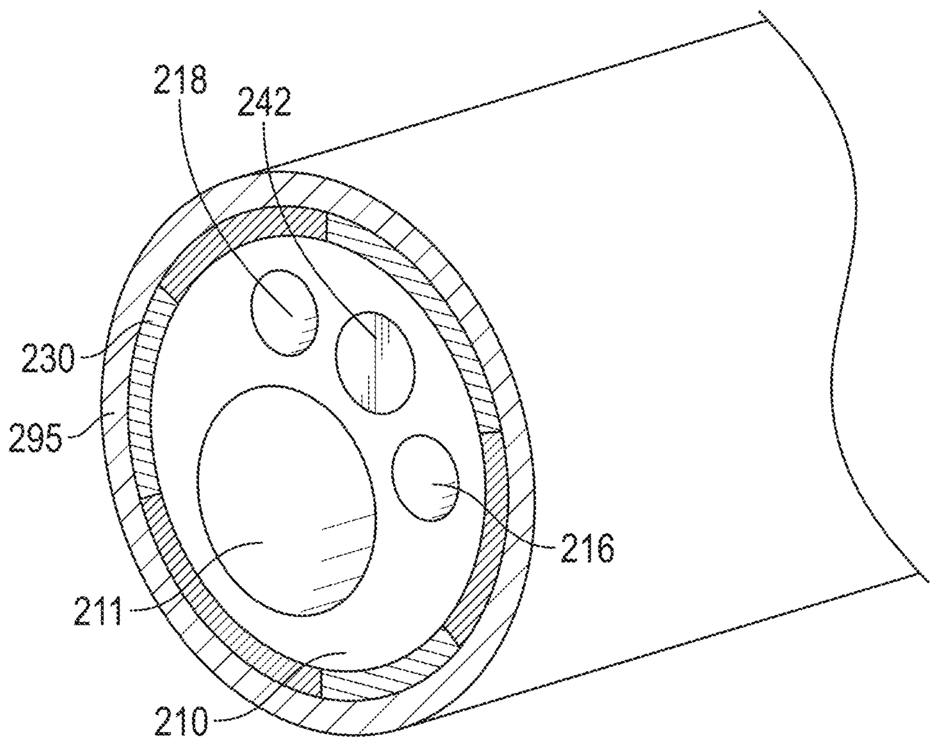
FIG. 2F is a cross-sectional perspective view of the catheter of FIG. 2E.

Returning to FIGS. 2B-2C, the guidewire sheath 210 provides various internal conduits connecting elements of the distal end 200 with the proximal end of the catheter (not pictured), including a guidewire lumen 211 for receiving a guidewire; a wire lumen 212 for carrying an insulated wire 242, and one or more fluid lumens 216, 218 for carrying a fluid, e.g., the conductive fluid, from a proximal end of the catheter to the cap 280. The internal structure of the guidewire sheath 210 is shown more clearly in FIGS. 2E-2F. FIG. 2E provides a cross-section of a more proximal section of the shaft of the catheter of FIGS. 2B-2C. FIG. 2F provides a perspective view of the cross-section of FIG. 2E inside of an outer jacket of the catheter 200.

As shown in FIG. 2E, the catheter includes a central, tubular guidewire sheath 210 defining a plurality of lumens. The plurality includes a first lumen (i.e., the guidewire lumen 211) for receiving a guidewire and a second lumen (i.e., the wire lumen 212) for carrying a conductive wire 242. The guidewire lumen 211 may extend through the center of the guidewire sheath 210, or may be slightly offset from the center as shown in FIG. 2E. The guidewire lumen 211 is shaped to loosely receive a guidewire having a diameter between approximately 0.014 inches and approximately 0.035 inches. The wire lumen 212 is shaped to carry at least one wire 242 for flowing current from the pulsed voltage source (such as the pulsed voltage source of FIG. 1A) to the electrode pairs at the distal end 200 of the catheter. In some examples, the wire is a polyimide insulated copper wire having a diameter between approximately 0.003 inches and approximately 0.007 inches. The wires may be flattened to reduce the profile of the catheter, with the flattened wires having a cross-section that is approximately 0.003 inches thick and approximately 0.010 inches wide. The plurality of lumens also includes a fluid inlet lumen 216 for flowing fluid into the cap 280 and a fluid outlet lumen 218 for flowing fluid out of the cap 280. While the lumens are pictured in FIG. 2E as having approximately circular cross-section, lumens in the guidewire sheath 210 may have any desired shape. For instance, the wire 242 could have a flattened shape and the second lumen 212 could have a flattened or oblong shape to accommodate the flattened wire. Similarly, the fluid inlet lumen 216 or the fluid outlet lumen 218 could be arranged around the circumference of the guidewire sheath (e.g., in an annular space between the sheath and the reinforced wire sheath 230). The location, size, and shape of any of the lumens can be modified to reduce the profile of the catheter or to provide some other benefit. Further, the various lumens may be combined (e.g. by providing two or more insulated wires in the same lumen) or eliminated without departing from the scope of the present invention.

Surrounding the guidewire sheath 210 is a tubular reinforced wire sheath 230 formed from at least one conductive reinforced wire material (e.g., a wire that is braided, coiled or both), for example, reinforced copper or stainless steel. As described previously with reference to FIG. 1A, the reinforced wire sheath 230 can be used to carry current from a pulsed voltage source at the proximal end of the catheter to the distal end 200 of the catheter to provide current to one or more electrode pairs. A proximal end of the reinforced wire sheath 230 is connectable to a pulsed voltage source, while the distal end of the reinforced wire sheath is connected to one or more of the electrode pairs. In some embodiments, the reinforced wire sheath 230 is connected to an electrode pair via a conductive piece of metal shaped to form an electrode (e.g., the conductive emitter portion 234 depicted in FIG. 2C). In addition to providing a current to the electrode pairs of distal end 200, the reinforced wire sheath 230 may also provide favorable mechanical properties to the shaft of the catheter. For instance, the material composition of the reinforced wire sheath 230 could provide increased torqueability, pushability, or enhanced rigidity to the catheter shaft to facilitate maneuvering the catheter through a patient's vasculature. In some embodiments, the reinforced sheath 230 includes one or more braided or coiled metals (e.g., metal wires) encapsulated at least partially in a polymer. Polymer encapsulation insulates the conductive metal elements of the sheath 230 and/or to provides improved mechanical properties. The reinforced metal of the sheath 230 may be flattened to reduce the profile of the sheath 230 and allow the catheter to more easily fit into tightly occluded vessels.

Returning to FIGS. 2B-2C, the distal end 200 of the catheter also includes a soft tip 290 that tapers toward the distal tip of the catheter. The soft tip 290 can be formed from a polymer or any other suitable biocompatible material. In a preferred embodiment, the tip 290 is formed at least partially from a radiopaque material such as platinum, iridium, or stainless steel to permit fluoroscopic viewing of the catheter during use. The soft tip also includes a guidewire lumen such that, during operation, the catheter is advanced through a patient's vasculature along a guidewire with the soft tip leading. Providing a soft tip 290 may prevent physical damage to blood vessel walls while facilitating contact with and entry into tight lesions in the vasculature.

The distal end 200 also includes the shock wave generator of the catheter, which includes a first electrode pair, shown in FIG. 2B and a second electrode pair shown in FIG. 2C. The electrode pairs have low-profile configurations (e.g., are coplanar or at least partially recessed into the guidewire sheath 210) to reduce the diameter of the distal end 200. The first electrode pair and the second electrode pair are located approximately 180 degrees apart circumferentially around the guidewire sheath 210. The electrodes of each pair are spaced apart to define gaps where current can flow to produce shock waves in the conductive fluid inside the flexible cap 280.

An electrode pair can be formed by a side edge of a conductive sheath (e.g., a ring electrode) and a conductive portion of a wire, as described in assignee's prior filing U.S. Pub. No. 2019/0150960. The conductive portion of the wire can be formed by removing a portion of the insulating layer of an insulated wire near the distal end of the wire to expose an electrically conductive portion of the wire. The location, size, and shape of the removed portion may vary to control the location, direction, and/or magnitude of the shock wave. In some embodiments, an electrode may be formed by cutting the end of an insulated wire to expose an electrically conductive cross-section. In some embodiments, flat wires rather than round wires are used to further reduce the crossing profile of the electrode assembly.

With reference to FIG. 2B, the first electrode pair includes a first electrode formed from an insulation removed portion 243 of a wire extending through a lumen 212 of the guidewire sheath 210, for instance, conductive wire 242. The first electrode pair also includes a second electrode formed from a cut out 222 in a conductive sheath 220 wrapped circumferentially around the guidewire sheath. The cut out 222 in the conductive sheath 220 is defined by an approximately circular hole in the conductive sheath. The location, size, and shape of the cut out 222 can be varied to control the location, direction, and/or magnitude of the shock wave. In some examples, the conductive sheath 220 is at least partially recessed into the guidewire sheath 210 to reduce the profile of the electrode assembly and the diameter of distal end 200 of the catheter.

The insulation removed portion 243 of the wire 242 and the cut out 222 of the conductive sheath 220 are spaced apart to define a gap between the first electrode and the second electrode of the first electrode pair. The spacing of the gap can be controlled to generate reproducible electrical arcs in the conductive fluid between the electrodes. The spacing of the electrodes may be modified to produce shock waves having a desired magnitude for a given voltage and current output from a pulsed voltage source. To permit current flow between the insulation removed portion 243 of the wire 242 in the lumen and the cut out 222 of the outer conductive sheath 220, the guidewire sheath 210 includes an aperture extending between the outer surface of the guidewire sheath and the wire lumen 212. The aperture is positioned over the insulation removed portion 243 of the wire 242 and under the cut out 222 such that current flows through the aperture when high voltage pulses are applied across the reinforced wire sheath 230 and the wire 242. The size of the aperture may correspond to the size of the insulation removed portion 243 of the wire 242, the size of the cut out 222 in the conductive sheath 220, or some other desired size or shape.

FIG. 2C provides a cross section of the distal end 200 of the catheter of FIG. 2B rotated by 180 degrees to show a second electrode pair of the shock wave generator. The second electrode pair includes a first electrode formed from an edge 224 of the conductive sheath 220, and a second electrode formed from a conductive emitter portion 234 coplanar with the conductive sheath 220. As shown in FIG. 2C, the first and second electrode of the second electrode pair are formed in a tongue-and-groove configuration. The edge 224 of the conductive sheath 220 is defined by a longitudinal cut in the side of the conductive sheath and forms the "groove". The "tongue" is formed from the conductive emitter portion 234, which extends into the groove such that the tongue and groove define a U-shaped gap between the emitter portion 234 and the edge 224 of the conductive sheath 220. The shape of the gap can be controlled to generate reproducible electrical arcs in the conductive fluid between the electrodes of the pair and to produce shock waves having a desired magnitude. The conductive sheath 220 and the emitter portion 234 are coplanar to reduce the profile of the electrode pair and the diameter of the distal end 200 of the catheter. In some embodiments, the conductive emitter portion 234 additionally includes PET heat shrink tubing. More information about tongue-and-groove electrode configurations is included in applicant's U.S. Pat. No. 10,555,744, incorporated herein by reference.

As shown in FIG. 2C, the emitter portion 234 is coupled to the distal end of the reinforced wire sheath 230, which electrically connects the second electrode pair with a pulsed voltage source (not pictured). However, in alternative embodiments the emitter portion 234 could be coupled to, e.g., a further wire extending along the catheter, which electrically connects the second electrode pair with the pulsed voltage source. Returning to FIG. 2B, the first electrode pair is electrically connected to the pulsed voltage source via the wire 242 extending within the lumen 212 of the guidewire sheath 210. The proximal end of the wire 242 is connectable to the pulsed voltage source, while the distal end of the wire 242 is connected to (i.e., forms a part of or is otherwise electrically connected with) the first electrode pair.

Figure 2G:
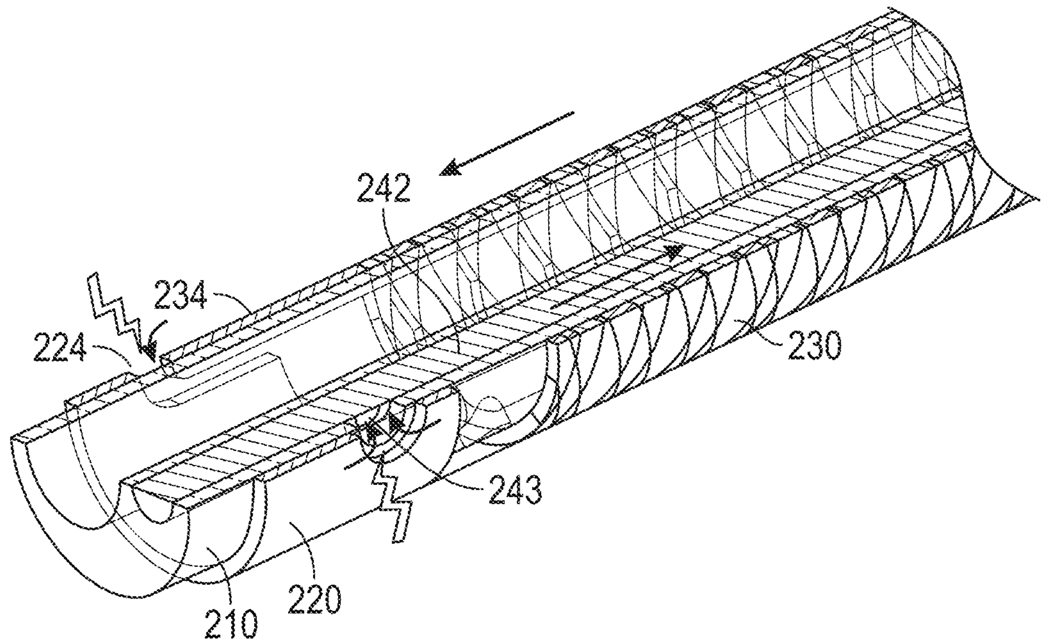
FIG. 2G is a longitudinal cutaway view of the catheter of FIG. 2A showing an electrical current flow through the catheter.

The wire 242 and the reinforced wire sheath 230 complete a circuit between the electrode pairs and the pulsed voltage source, such that when high voltage pulses are applied across the reinforced wire sheath 230 and the wire 242, current flows across the gaps between the electrodes of the first electrode pair and the second electrode pair creating shock waves for treating an occlusion. FIG. 2G shows show an exemplary current flow through a catheter having one tongue-and-groove electrode pair and one dot-circle electrode pair connected to a voltage source by way of a polyimide-insulated copper wire and a reinforced wire sheath formed of flat copper clad stainless steel wire.

In operation, a physician may simultaneously connect the wire 242 to a positive lead of the voltage pulse generator, and connect the reinforced wire sheath 230 (or a wire electrically connected to a proximal end of the sheath) to a negative lead or the ground. In such an example, current will flow from the voltage source, down the wire 242, across the first gap between the insulation removed portion 243 of the wire and the cut out 222 in the conductive sheath 220, creating a plasma arc that generates a shock wave at the first electrode pair. The current then flows across the conductive sheath 220 and across the second gap between the edge 224 of the conductive sheath 220 and the conductive emitter portion 234, creating another plasma arc that generates a shock wave at the second electrode pair. The current then flows from the conductive emitter portion 234 to the reinforced wire sheath 230, and down the reinforced wire sheath to reach the negative lead or ground. Alternatively (as seen in FIG. 1G), the physician may connect the reinforced wire sheath 230 (or a wire electrically connected to the reinforced wire sheath) to a positive lead of the pulse generator and connect the wire 242 to the negative lead or ground, such that the current travels the opposite path across the first and second electrode pairs.

Figure 3A:
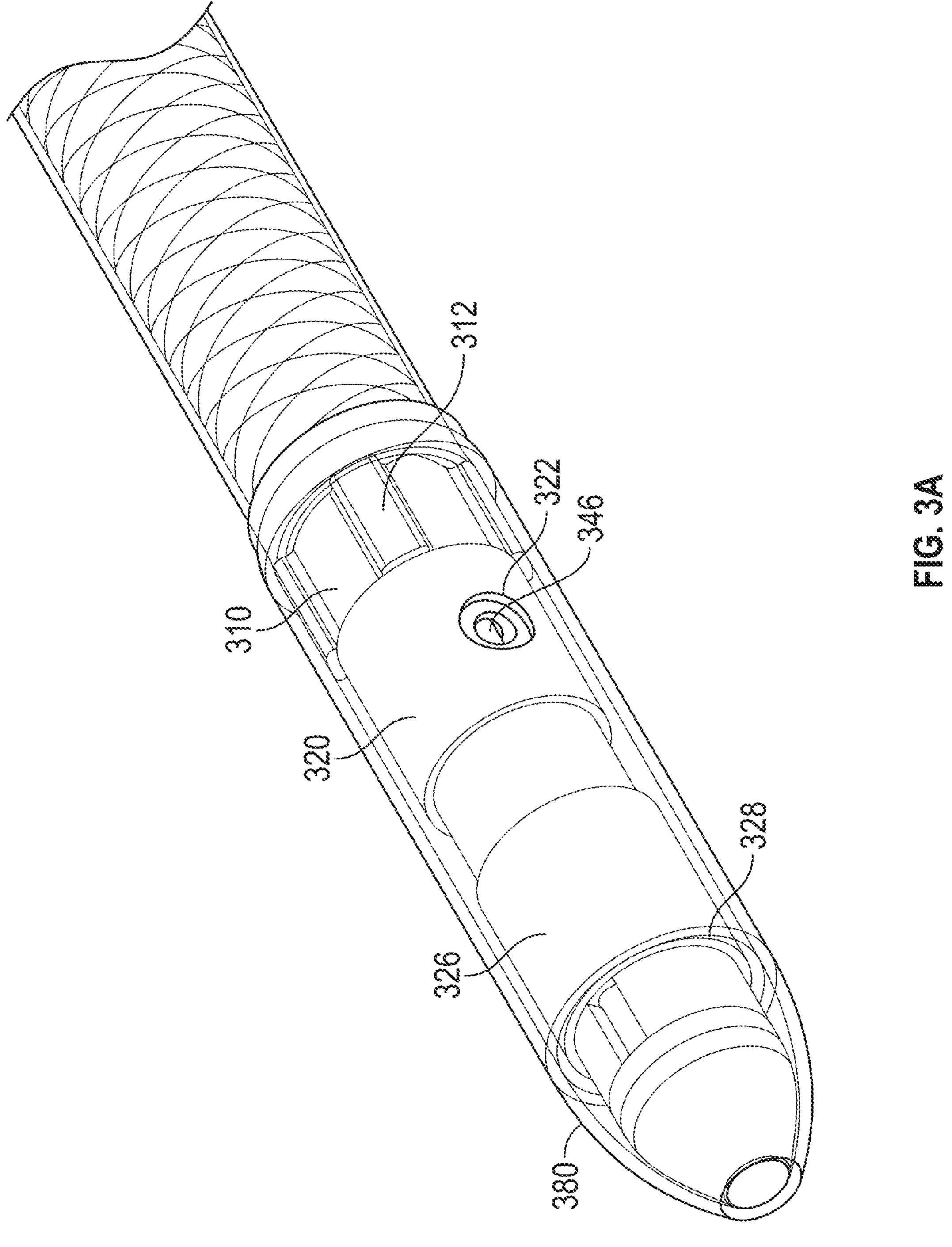
FIG. 3A is a perspective view of a distal section of a catheter according to another embodiment of the subject invention.

FIGS. 3A-3H provide detailed views of the distal end of an alternative catheter that can be included in a shock wave angioplasty device, such as any of the catheters of FIGS. 1A-1E and described herein. Unlike FIGS. 2A-2G, the distal end 300 shock wave generator of catheter of FIGS. 3A-3H includes at least one distal emitter (e.g., one or more distal electrode pairs) and at least one proximal emitter (e.g., one or more proximal electrode pairs). FIG. 3A provides a perspective view of an exemplary catheter including a distal emitter and a proximal emitter. As illustrated in FIG. 3A, the distal emitter and the proximal emitter are formed from a respective proximal conductive sheath (e.g., a proximal electrode ring) and distal conductive sheath (e.g., a distal electrode ring) wrapped circumferentially around a guidewire sheath. The distal emitter includes one or more distal electrode pairs, while the proximal emitter includes one or more proximal electrode pairs. The electrode pairs have a low profile-configuration and are electrically connected to an external pulsed voltage source by way of a number of conductive wires extending through lumens of the guidewire sheath.

Figure 3B:
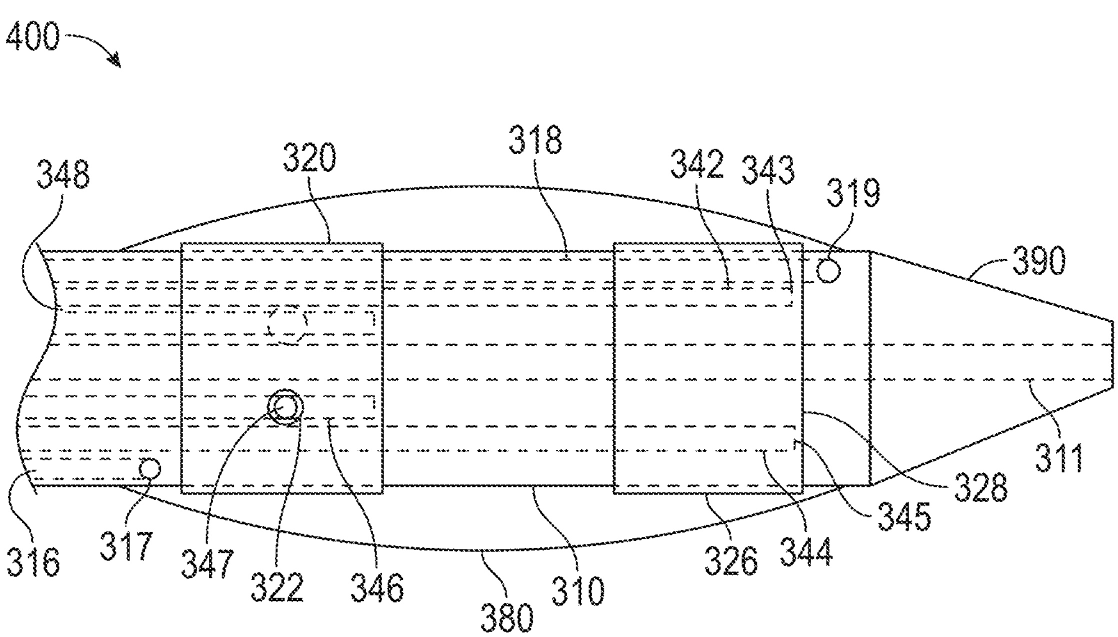
FIG. 3B is a side view illustration of the distal end of the catheter of FIG. 3A including a first distal electrode pair and a first proximal electrode pair and a no-fold balloon over the electrode pairs.
Figure 3C:
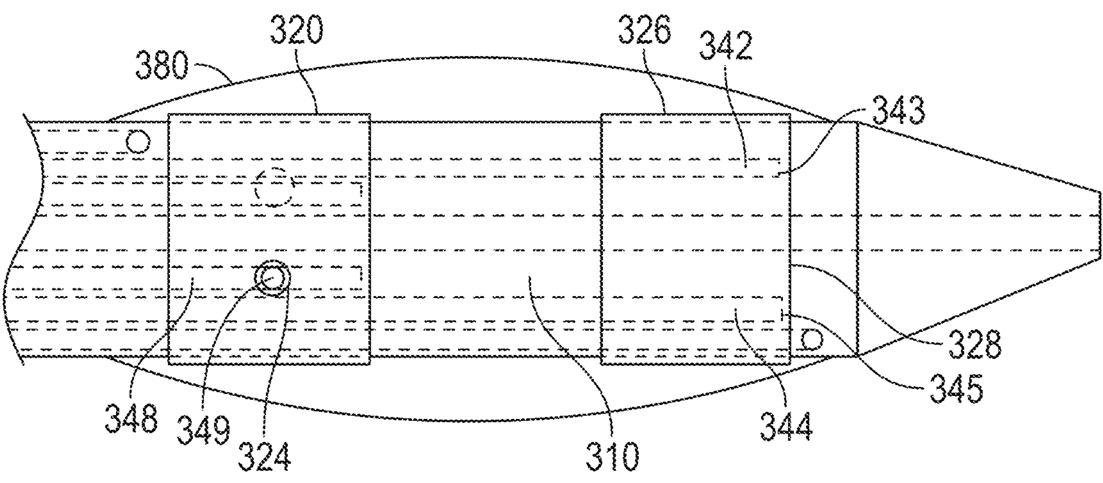
FIG. 3C is an illustration of the embodiment of FIG. 3B rotated by 180 degrees to show a second distal electrode pair and a second proximal electrode pair.

FIG. 3B depicts a first side of the distal end 300 of an exemplary catheter showing a first distal electrode pair and a first proximal electrode pair. FIG. 3C provides a second view of the distal end 300 of the catheter of FIG. 3B rotated 180 degrees to show a second distal electrode pair and a second proximal electrode pair. As shown in FIGS. 3B-3C, the distal end 300 of the catheter includes a guidewire sheath 310, a shockwave generator including two distal electrode pairs and two proximal electrode pairs, and a flexible cap 380 surrounding the electrode pairs. The flexible cap 380 is wrapped circumferentially around the guidewire sheath 310 and sealed to the distal end 300 of the catheter using, e.g., an adhesive seal or a thermal seal to form a closed annular channel around the guidewire sheath 310. In some embodiments, the flexible cap 380 is a no-fold angioplasty balloon (i.e. a low-profile angioplasty balloon) that can be positioned in a patient's vasculature without folding. When the balloon 380 is in a deflated state (see, e.g. FIG. 1B), the surface area of the balloon is small enough that the balloon is not folded when the catheter is advanced into a blood vessel. In some examples, the flexible cap 380 is an extruded tubular structure formed of a semi-compliant polymer material (i.e., an extruded polymer tube). The semi-compliant polymer material allows the flexible cap 380 to inflate slightly responsive to fluid pressure inside the flexible cap, and then return to its original size when under no pressure.

The flexible cap 380 is inflatable with a conductive fluid, for example, saline, such that the cap expands to provide a space between the inner wall of the cap and the proximal and distal electrode pairs (see, e.g., FIG. 1C). In some embodiments, the flexible cap 380 expands a relatively small amount such that the inflated cap retains a low profile (e.g., has a diameter less than 1 millimeter). For example, the maximum inflated diameter of the flexible cap 380 may be no more than 10%-15% greater than the original (i.e., deflated) diameter of the cap. However, when inflated, the flexible cap 380 should provide a space sufficient to allow the conductive fluid to surround and immerse the electrode pairs to avoid damage to the cap during shock wave generation. When inflated, the conductive fluid allows the acoustic shock waves from the proximal and distal electrode pairs to propagate through the walls of the flexible cap 380 and into a lesion in contact with the outer surface of the cap. In some embodiments, the conductive fluid also contains an x-ray contrast agent to permit fluoroscopic viewing of the catheter during IVL treatment.

Figure 3D:
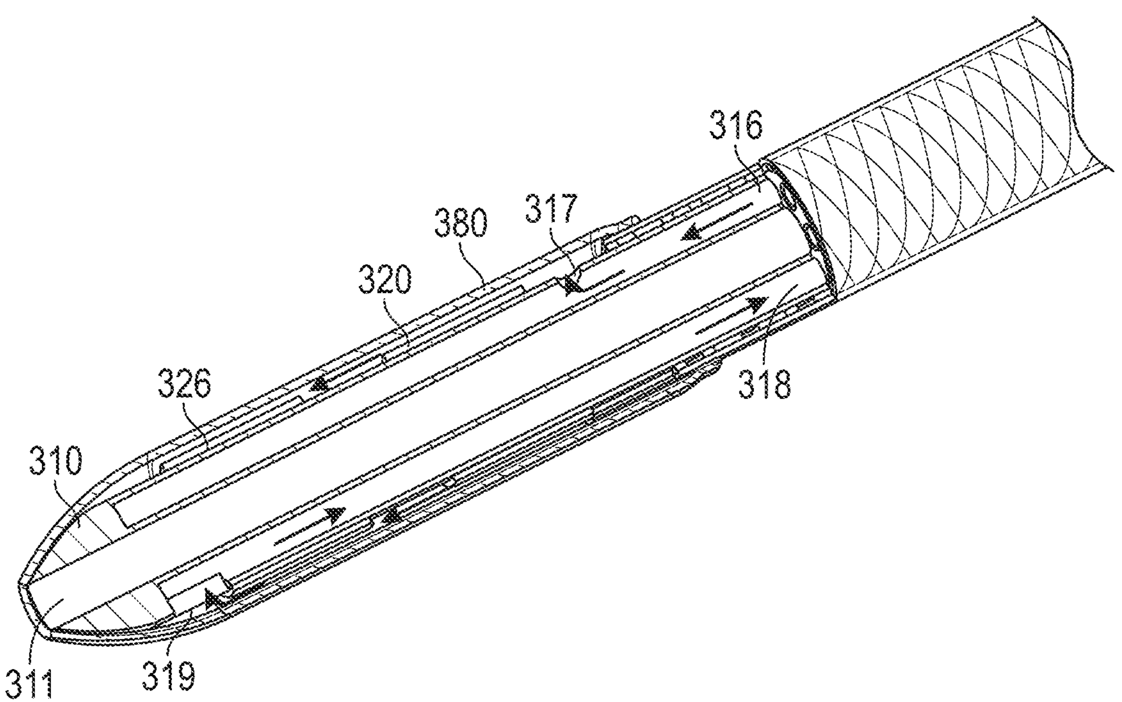
FIG. 3D is a longitudinal cross section of a distal section of the catheter of FIG. 3A showing a fluid path for a conductive fluid

The conductive fluid is admitted into the cap 380 via a fluid inlet 317 in the guidewire sheath 310, and removed from the cap via a fluid outlet 319 in the guidewire sheath. The fluid inlet 317 and fluid outlet 319 provide channels extending from the surface of the guidewire sheath 310 to a respective fluid inlet lumen 316 and fluid outlet lumen 318 in the guidewire sheath (and, more proximally, allow the flexible cap to access fluid supplied by the fluid port shown in FIG. 1A). While treating an occlusion, fluid can be continually flushed through the cap 380 via the inlet 317 and the outlet 319 to clear bubbles and debris produced when high voltage pulses across the electrodes create shock waves in the cap. The fluid inlet 317 and fluid outlet 3219 are positioned to maximize fluid flow across the electrode pairs, such that fluid flowed through the cap 380 via the inlet and outlet flows across at least one of the electrode pairs. For example, as depicted in FIG. 3A, the fluid inlet 317 and the fluid outlet 319 can be positioned diagonally across one or more of the conductive sheaths 330, 336, such that one or more of the electrode pairs are positioned between the fluid inlet and the fluid outlet. FIG. 3D provides a cross-sectional view of a distal section of an exemplary catheter depicting the flow of fluid through internal lumens and the flexible cap of the catheter via a fluid inlet and a fluid outlet in the guidewire sheath.

As illustrated in FIGS. 3A-3D, the guidewire sheath 310 provides various internal conduits connecting elements of the distal end with the proximal end of the catheter, including a guidewire lumen, lumens for carrying conductive wires, and one or more fluid lumens. The internal structure of the guidewire sheath 310 is shown more clearly in FIGS. 3E, which provides a cross-section of a more proximal section of the shaft of the catheter. FIG. 3F provides a perspective view of the cross-section of FIG. 3E inside of the flexible cap 380 the catheter 300.

Figure 3E:
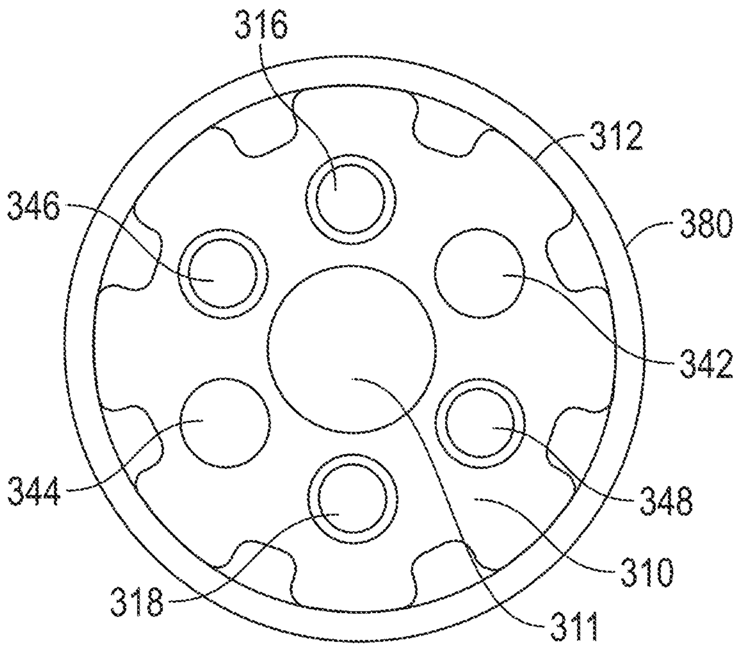
FIG. 3E is a cross-sectional view of the embodiment of FIGS. 3B-3C, taken at a more proximal region of the catheter.
Figure 3F:
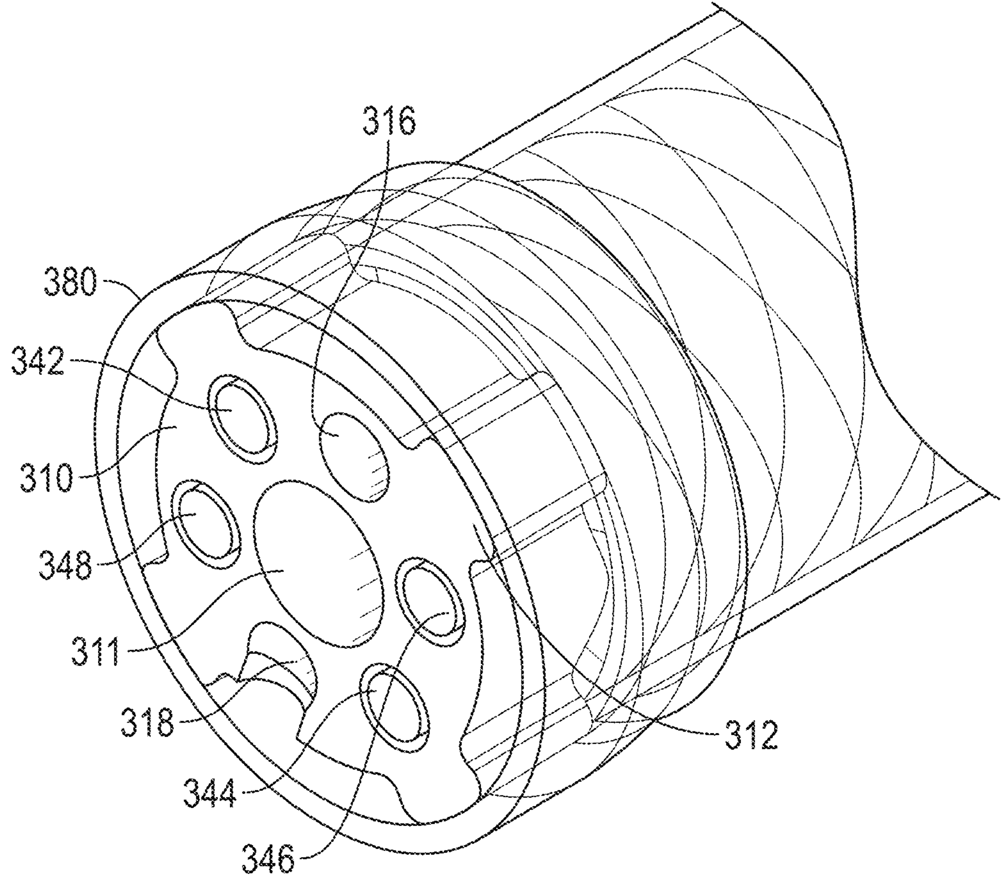
FIG. 3F is a cross-sectional perspective view of the catheter of FIG. 3E.

As shown in FIG. 3E, the catheter includes a central, tubular guidewire sheath 310 defining a plurality of lumens. The plurality of lumens includes a guidewire lumen 311 for receiving a guidewire. The guidewire lumen 311 may extend through the center of the guidewire sheath 310, as shown in FIGS. 3E-3F, or may be slightly offset from the center. The guidewire lumen 311 is shaped to loosely receive a guidewire having a diameter between approximately 0.014 inches and approximately 0.035 inches. The guidewire sheath 310 also includes four wire lumens for carrying respective conductive wires 342, 344, 346, 348 for flowing current from a pulsed voltage source (such as the pulsed voltage source of FIG. 1A) to the proximal and distal electrode pairs. In some examples, the wires 342, 344, 346, 348 are polyimide insulated copper wires having a diameter between approximately 0.003 inches and approximately 0.007 inches. The wires 342, 344, 346, 348 may be flattened to reduce the profile of the catheter, with the flattened wires having a cross-section that is approximately 0.003 inches thick and approximately 0.010 inches wide. The plurality of lumens also includes a fluid inlet lumen 316 for flowing fluid into the cap 380 and a fluid outlet lumen 318 for flowing fluid out of the cap 380. While the lumens are pictured in FIGS. 3E-3F as having approximately circular cross-sections, lumens in the guidewire sheath 310 may have any desired shape. For instance, one or more of the wires 342, 344, 346, 348 could have a flattened shape and the associated lumen could have a flattened or oblong shape to accommodate the flattened wire. Similarly, the fluid inlet lumen 316 or the fluid outlet lumen 318 could be arranged around the circumference of the guidewire sheath 310 (e.g., in an annular space between the sheath and the reinforced wire sheath 330). The location, size, and shape of any of the lumens can be modified to reduce the profile of the catheter or to provide some other benefit. Further, the various lumens may be combined (e.g. by providing two or more insulated wires in the same lumen) or eliminated without departing from the scope of the present invention.

As shown in FIGS. 3E-3F, at least a portion of the guidewire sheath 310 includes spacing features 312 that protrude from an outer surface of the guidewire sheath. The spacing features 312 are configured to maintain the inner surface of the cap 380 a controlled distance away from the outer surface of the guidewire sheath 310, e.g., in order to prevent damage to the cap caused by the shock waves produced at the electrode pairs. In some embodiments, the spacing features 312 surround one or more of the conductive sheaths 320, 326, or extend between the respective proximal conductive sheath 320 and the distal conductive sheath 326

Returning to FIGS. 3B-3C, the distal end 300 of the catheter also includes a soft tip 390 that tapers toward the distal tip of the catheter. The soft tip 390 can be formed from a polymer or any other suitable biocompatible material. In a preferred embodiment, the tip 390 is formed at least partially from a radiopaque material such as platinum, iridium, or stainless steel to permit fluoroscopic viewing of the catheter during use. The soft tip also includes a guidewire lumen such that, during operation, the catheter is advanced through a patient's vasculature along a guidewire with the soft tip leading. Providing a soft tip 390 may prevent physical damage to blood vessel walls while facilitating contact with and entry into tight lesions in the vasculature.

The distal end 300 also includes the shock wave generator of the catheter, which includes a first distal electrode pair and a first proximal electrode pair, shown in FIG. 3B and a second distal electrode pair and a second proximal electrode shown in FIG. 3C. The first and second distal electrodes are formed from respective conductive portions 343, 355 of a first wire 342 and a second wire 344 and a distal conductive sheath 326 (e.g., a distal ring electrode), while the first and second proximal electrode pairs are dot-circle electrode pairs formed from insulation removed portions of a third wire 346 and fourth wire 348 and a proximal conductive sheath 320. The electrode pairs have low-profile configurations to reduce the diameter of the distal end 300. For instance, the proximal conductive sheath 320 and/or the distal conductive sheath 326 may be at least partially recessed into the guidewire sheath 310 to reduce the diameter of the distal end 300 of the catheter.

As mentioned above, an electrode pair can be formed by a side edge of a conductive sheath and a portion of a wire. The portion of wire can be formed by removing a portion of the insulating layer of a wire near the distal end of the wire to expose an electrically conductive portion of the wire. The location, size, and shape of the removed portion may vary to control the location, direction, and/or magnitude of the shock wave. In some embodiments, an electrode may be formed by cutting the end of an insulated wire to expose an electrically conductive cross-section. In some embodiments, flat wires rather than round wires are used to further reduce the crossing profile of the electrode assembly.

With reference to FIG. 3B, the first distal electrode pair includes a first electrode formed from a conductive portion 343 of a first wire 342 extending through a lumen of the guidewire sheath 310. The first distal electrode pair also includes a second electrode formed from a side edge 328 of a distal conductive sheath 326 wrapped circumferentially around the guidewire sheath 310. With reference to FIG. 3C, the second distal electrode pair includes a first electrode formed from the side edge 328 of the distal conductive sheath 326. The second distal electrode pair also includes a second electrode formed from a conductive portion 345 of a second wire 344 extending through a lumen of the guidewire sheath 310. The first distal electrode pair and the second distal electrode pair are located approximately 180 degrees apart circumferentially around the distal conductive sheath 326.

The conductive portion 343 of the first wire 342 is spaced apart from the side edge 328 of the distal conductive sheath 326 to define a first gap between the electrodes of the first distal pair. Likewise, the conductive portion 345 of the second wire 344 is spaced apart from the side edge 328 of the distal conductive sheath 326 to define a second gap between the electrodes of the second distal pair. The spacing of the gaps can be controlled to generate reproducible electrical arcs in the conductive fluid between the electrodes of the respective pairs and to produce shock waves having a desired magnitude for a given voltage and current output from the pulsed voltage source. To permit current flow between the conductive portions 343, 345 of the wires 342, 344 and the distal conductive sheath 326, the guidewire sheath 310 includes distal apertures extending between the outer surface of the guidewire sheath 310 and the lumens containing the first wire 342 and the second wire 344. The apertures are positioned between the conductive portions 343, 345 of the wires 342, 344 and the side edge 328 of the distal conductive sheath 326 such that current flows through the respective apertures when high voltage pulses are applied across the first wire 342 and the second wire 344.

Returning to FIG. 3B, the first proximal electrode pair includes a first electrode formed from an insulation removed portion 347 of a third wire 346 extending through a lumen of the guidewire sheath 310. The first proximal electrode pair also includes a second electrode formed from a first cut out 322 in the proximal conductive sheath 320. With reference to FIG. 3C, the second proximal electrode pair includes a first electrode formed from an insulation removed portion 349 of a fourth wire 348 extending through a lumen of the guidewire sheath 310. The second proximal electrode pair also includes a second electrode formed from a second cut out 324 in the proximal conductive sheath 320. The first proximal electrode pair and the second proximal electrode pair are located approximately 180 degrees apart circumferentially around the proximal conductive sheath 320.

The insulation removed portion 347 of the third wire 346 is spaced apart from the first cut out 322 of the proximal conductive sheath 320 to define a first gap between the electrodes of the first proximal pair. Likewise, the insulation removed portion 349 of the fourth wire 348 is spaced apart from the second cut out 324 of the proximal conductive sheath 320 to define a second gap between the electrodes of the second proximal pair. The spacing of the gaps can be controlled to generate reproducible electrical arcs in the conductive fluid between the electrodes of the respective pairs and to produce shock waves having a desired magnitude for a given voltage and current output from the pulsed voltage source. To permit current flow between the insulation removed portions 347, 349 of the wires 346, 348 in the lumens and the external cut outs 322, 324 in the proximal conductive sheath 320, the guidewire sheath 310 includes proximal apertures extending between the outer surface of the guidewire sheath 310 and the lumens containing the third wire 346 and the fourth wire 348. The apertures are positioned between the insulation removed portions 347, 349 of the wires 346, 348 and the cut outs 322, 324 in the proximal conductive sheath 320 such that current flows through the respective apertures when high voltage pulses are applied across the third wire 346 and the fourth wire 348.

As shown in FIGS. 3B-3C, the distal ends of the first wire 342 and the second wire 344 are connected to (i.e., form a part of or are electrically connected with) the distal electrode pairs and the proximal ends of the first wire 342 and the second wire 344 (not shown) are connectable to a pulsed voltage source, such that when high voltage pulses are applied across the first wire 342 and the second wire 344, current flows across the first gap and the second gap creating shock waves for treating occlusions near the distal electrodes. Likewise, the distal ends of the third wire 346 and the fourth wire 348 are connected to the proximal electrode pairs and the proximal ends of the third wire 346 and the fourth wire 348 are connectable to the pulsed voltage source, such that when high voltage pulses are applied across the third wire 346 and the fourth wire 348, current flows across the first gap and the second gap creating shock waves for treating occlusions near the proximal electrodes.

Figure 3G:
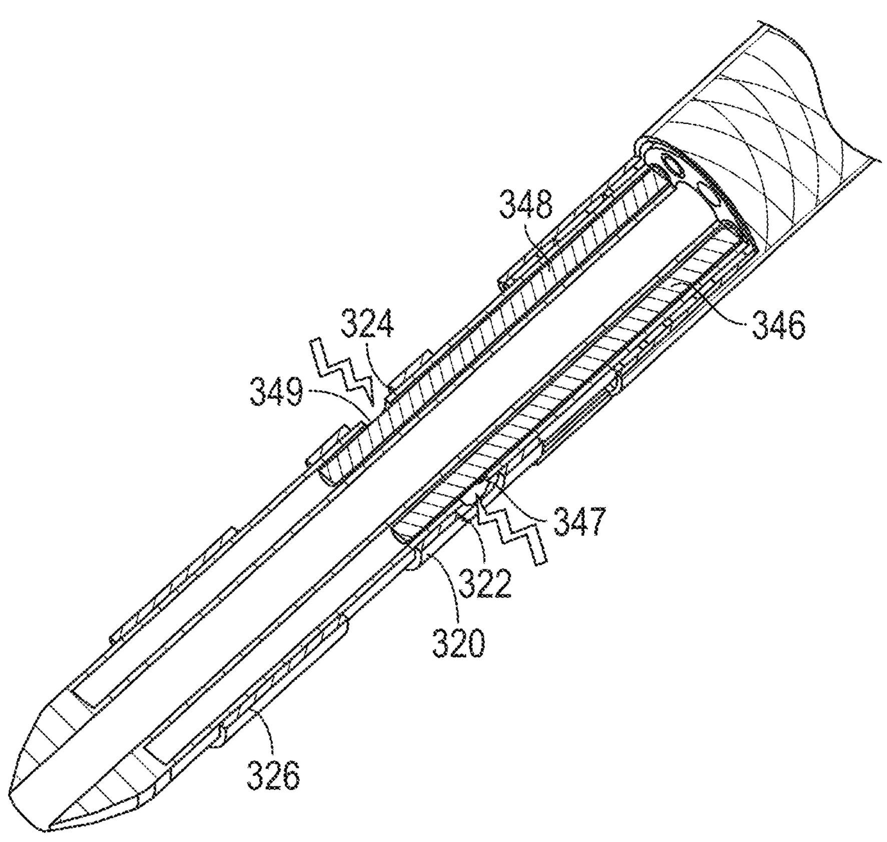
FIG. 3G provides a cross-sectional view of the catheter of FIG. 3A being used to generate shock waves at a proximal emitter.
Figure 3H:
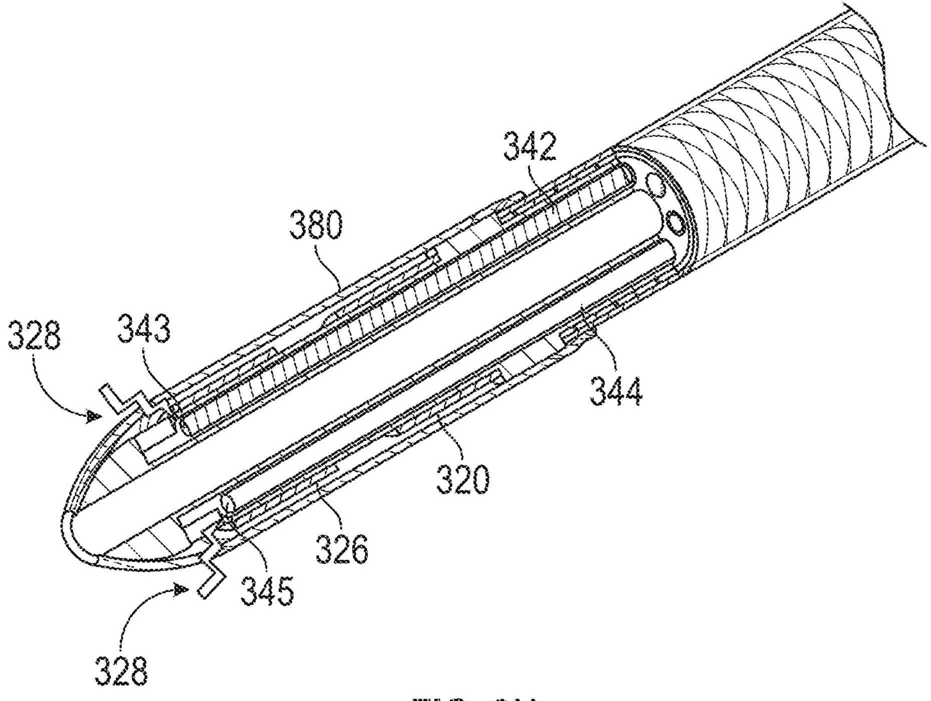
FIG. 3H provides a perpendicular cross-sectional view of the catheter of FIG. 3G being used to generate shock waves at a distal emitter.

In operation, a physician may want to independently control the distal and proximal electrode pairs to selectively generate shock waves in different portion of the cap 380. FIG. 3G illustrates the selective firing of the proximal emitters by applying a current to the proximal emitter wires. FIG. 3H illustrates the selective firing of the distal emitters by applying a current to the distal emitter wires. The separate wiring of the proximal and distal electrode pairs advantageously allows for generation of either distal or proximal shock waves by applying high voltage pulses across only the wires corresponding to the proximal or distal electrodes. In other words, the pulsed voltage source can be controllable to apply high voltage pulses across either the first wire 342 and the second wire 344 to create shock waves at the distal electrode pairs or the third wire 346 and the fourth wire 348 to create shock waves at the proximal electrode pairs.

It should be noted that the elements and features of the example catheters illustrated in FIGS. 2A-2G and FIG. 3A-3H may be rearranged, recombined, and modified without departing from the present invention. For instance, while FIGS. 2A-2G provide a catheter including a reinforced wire sheath, the reinforced wire sheath may be replaced by one or more conductive wires, as seen in the catheter of FIGS. 3A-3H. Relatedly, one or more of the wires in FIGS. 3A-3H could be replaced by a reinforced wire sheath. Similarly, features of the embodiment of FIGS. 3A-3H, e.g., the spacing features, a further proximal conductive sheath, additional electrode pairs and/or independently controlled distal and proximal electrode pairs, may be combined with the catheter of FIGS. 2A-2G without departing from the subject invention.

Further, while FIGS. 2A-2G and 3A-3H illustrate two examples of shock wave generators, the subject invention is intended to include catheters having a variety of electrode configurations. For instance, a shock wave generator of an exemplary catheter could include two tongue-and-groove electrode pairs (see FIGS. 2B and 5A-5C), two dot and circle electrode pairs (see FIG. 2C and the proximal electrode pairs of FIGS. 3B-3C), or two electrode pairs formed from distal conductive portions of wires and a conductive sheath (see, e.g., the distal electrode pairs of FIGS. 3B-3C), or any other desired configuration. Further, the placement and spacing of the electrode pairs can modified without departing from the subject invention. For instance, the electrode pairs may be spaced circumferentially around the catheter in consistent increments, e.g., 180 degrees apart, 90 degrees apart, or 60 degrees apart to generate shock waves more evenly around the catheter. In some examples, such as the embodiment shown in FIGS. 3A-3H, the shock wave generator includes electrode pairs positioned in various groupings spaced longitudinally along the catheter. For example, the shock wave generator could include a plurality of electrode pairs defined by a plurality of conductive sheaths spaced longitudinally along the catheter.

FIGS. 4A-4B, 5A-5C, and 6A-6B depict several exemplary shock wave electrode assemblies that could be included in a shock wave angioplasty device, such as any of the catheters illustrated in FIGS. 1A-1C, 2A-2G, and 3A-3H and described herein.

FIGS. 4A and 4B illustrate one exemplary variation of an electrode pair. This embodiment includes a pair of spaced apart ring electrodes provided as a first conductive sheath **52*b* and a second conductive sheath 58*c* wrapped circumferentially around the shaft of a catheter. One or more of the sheaths 58*c*, 52*b* may be recessed into the shaft to reduce the diameter of shock wave generator and to permit entry of the catheter into tighter lesions. In this example, an electrode pair is formed from respective side edges of the first conductive sheath 52*b* and the second conductive sheath 58*c*. The spacing between the side edges of the two conductive sheaths defines a spark gap 64 between the electrodes. FIG. 4B illustrates a different view of the electrodes of FIG. 4A, with the gap 64 shown larger for clarity. A first wire "A" 36 is connected to the first conductive sheath 52*b* and the second wire "B" is connected to ring electrode 58*c*. When a high voltage pulse is applied across the first wire "A" 36 and the second wire "B", a plasma arc is created across the spark gap 64** between the ring electrodes. The plasma arc creates a shock wave for treating an occlusion.

FIGS. 5A, 5B, and 5C illustrate exemplary tongue-and-groove electrode pair configurations formed a conductive sheaths (e.g., ring electrodes) and conductive emitter portions extending into the conductive sheaths. In these examples, a first electrode of the pair is formed from an edge of the conductive sheath that is defined by a groove cut into a side of the conductive sheath. The second electrode of the pair is formed from a conductive tongue-shaped emitter portion extending into the groove. The conductive emitter portion "tongue" may be formed from a conductive portion of a wire (for instance, an insulation removed portion or a conductive end of wire) or some other conductive metal portion shaped to fit within the groove. The tongue and groove define a U-shaped spark gap between the electrodes of the pair. As illustrated in FIG. 5B, a first wire 36 is connected to the conductive emitter portion "tongue" 52 and a second wire 38 is connected to the ring electrode conductive sheath 58. When a high voltage pulse is applied across the first wire 36 and the second wire 38, a plasma arc is created across the spark gap 64 between the tongue 52 and groove 60. The plasma arc creates a shock wave for treating the stenosis.

FIG. 5C illustrates a related exemplary tongue-and-groove electrode embodiment providing two electrode pairs formed from a single conductive sheath **58*a* (e.g., a single ring electrode) wrapped circumferentially around the guidewire sheath. As shown in FIG. 5C, a first groove 60*a* and a second groove 60*b* are cut into edges the same conductive sheath 58*a*. The first and second groove may be located 180 degrees circumferentially apart around the conductive sheath. Corresponding conductive tongue-shaped emitter portions extend into the first groove and second groove to create first and second electrode pairs. A first electrode pair is formed from the edge of the conductive sheath defined by the first groove 60*a* and the first tongue-shaped emitter portion 68** extending into the first groove.

The second electrode pair is formed from the edge of the conductive sheath defined by the second groove 60*b* and the second tongue-shaped emitter portion 52 extending into the second groove. Each electrode pair defines a U-shaped gap between the respective tongues and grooves of the first and second electrode pairs. In such an example, a first wire 38 is connected to the first emitter portion "tongue" 68 and a second wire 36 is connected to the second emitter portion "tongue" 52. When a high voltage pulse is applied across the first wire 38 and the second wire 36, current flows down the first wire 38 and jumps the first U-shaped gap, creating a first plasma arc. The current then travels along the conductive sheath 58*a* and jumps the second U-shaped gap, creating a second plasma arc, before traveling back to the voltage source along the second wire 36. The first and second plasma arcs create shock waves at two locations around the guidewire sheath, providing more complete circumferential treatment of a lesion in vasculature. More information and examples of tongue-and-groove electrode configurations can be found in U.S. Pat. No. 10,555,744, incorporated herein by reference.

FIGS. 6A and 6B illustrate another variation of an electrode pair of the subject invention. In this case, the first wire 36 and the second wires 38 are helically wrapped around the shaft of a catheter. One or more electrode pairs are created by selectively removing insulation from the wires to define electrodes. For example, a first electrode pair comprises a first insulation removed portion of the first wire 36 and a first insulation removed portion of the second wire 38. Further electrode pairs can be created by removing additional portions of insulation from the wires (i.e., such that a second electrode pair comprises a second insulation removed portion of the first wire and a second insulation removed portion of the second wire, etc.) The helically wrapped first wire 36 and second wire 38 are spaced sufficiently close to allow spark formation between the insulation removed portions of the two wires. The spaces between the insulation removed portions define spark gaps between respective electrode pairs. Examples of helically wound wires to create electrode pairs and more information can be found in U.S. Pat. No. 9,993,292 and U.S. Publication No. 2018/0098779, incorporated herein by reference.

It is noted that in the designs described above in reference to FIGS. 4A-4B, 5A-5C, and 6A-6B, the electrodes are arranged in the same plane (i.e., coplanar), thereby minimizing the diameter of the distal end of the catheter. Other suitable coplanar electrode designs are described in U.S. 2017/0135709, incorporated herein by reference.

It will be understood that the foregoing is only illustrative of the principles of the invention, and that various modifications, alterations and combinations can be made by those skilled in the art without departing from the scope and spirit of the invention. Any of the variations of the various shock wave catheters disclosed herein can include features described by any other shock wave catheters or combination of shock wave catheters herein. Furthermore, any of the methods can be used with any of the shock wave devices disclosed. Accordingly, it is not intended that the invention be limited, except as by the appended claims.

The invention claimed is:

1. A catheter for treating occlusions in blood vessels comprising:

a tubular guidewire sheath defining a first lumen for receiving a guidewire and a second lumen;

a shock wave generator located near a distal end of the catheter, said shock wave generator including at least one electrode pair, with electrodes of the at least one electrode pair being spaced apart to define at least one gap;

a first wire extending within the second lumen, with a proximal end of the first wire being connectable to a pulsed voltage source and with a distal end of the first wire being connected to a first electrode of the at least one electrode pair;

a reinforced wire sheath wrapped circumferentially around the tubular guidewire sheath, wherein a proximal end of the reinforced wire sheath is connectable to the pulsed voltage source and a distal end of the reinforced wire sheath is connected to a second electrode of the at least one electrode pair;

a distal tip positioned at the distal end of the catheter, the distal tip including a lumen for receiving the guidewire; and a cap having a distal end sealably attached to the distal tip and a proximal end sealably attached to the tubular guidewire sheath, the cap surrounding the at least one electrode pair to define a chamber fillable with conductive fluid, wherein when the chamber is filled with the conductive fluid and high voltage pulses are applied across the reinforced wire sheath and the first wire, current flows across the at least one gap creating shock waves for treating an occlusion.

2. The catheter of claim 1, wherein the cap is flexible and can be expanded by inflation with the conductive fluid and wherein a maximum inflated diameter of the cap is no more than 15% greater than a deflated diameter of the cap.

3. The catheter of claim 1, wherein the cap is made of material having elastomeric properties such that, after being inflated, the cap returns to a low profile configuration when deflated.

4. The catheter of claim 1, wherein the at least one electrode pair comprises a first electrode pair, the first electrode pair comprising:

an insulation removed portion of the first wire; and a cut out in a conductive sheath wrapped circumferentially around the tubular guidewire sheath.

5. The catheter of claim 4, wherein the cut out is defined by a hole in the conductive sheath.

6. The catheter of claim 4, wherein the tubular guidewire sheath comprises an aperture extending between an outer surface of the tubular guidewire sheath and the second lumen, wherein the aperture is positioned over the insulation removed portion of the first wire such that current flows through the aperture when the high voltage pulses are applied across the reinforced wire sheath and the first wire.

7. The catheter of claim 4, wherein the at least one electrode pair comprises a second electrode pair, the second electrode pair comprising:

an edge of the conductive sheath; and a conductive emitter portion coplanar with the conductive sheath, wherein the emitter portion is electrically coupled to the reinforced wire sheath.

8. The catheter of claim 7, wherein the edge of the conductive sheath comprises a groove, and wherein the emitter portion comprises a coplanar tongue extending into the groove such that the tongue and groove define a U-shaped gap between the emitter portion and the edge of the conductive sheath.

9. The catheter of claim 7, wherein the first electrode pair and the second electrode pair are located approximately 180 degrees apart circumferentially around the conductive sheath.

10. The catheter of claim 1, wherein the tubular guidewire A sheath further defines one or more fluid lumens for carrying the conductive fluid between a proximal end of the catheter and the cap.

11. The catheter of claim 1, wherein the tubular guidewire sheath comprises a fluid inlet for flowing the conductive fluid into the cap and a fluid outlet for flowing the conductive fluid out of the cap, and wherein the at least one electrode pair is positioned between the fluid inlet and the fluid outlet such that the conductive fluid flowed through the cap flows across the at least one electrode pair.

12. The catheter of claim 1, wherein the reinforced wire sheath comprises at least one braided or coiled metal wire encapsulated in a polymer.

13. The catheter of claim 12, wherein the metal wire is flattened to reduce a profile of the reinforced wire sheath.

14. The catheter of claim 12, wherein the metal wire comprises at least one of copper and stainless steel.

15. The catheter of claim 1, wherein the distal tip is a soft tip that tapers toward the distal end of the catheter.

* * * * *